United States Patent [19]

Green et al.

[11] Patent Number: 4,616,650
[45] Date of Patent: Oct. 14, 1986

[54] APPARATUS FOR APPLYING SURGICAL CLIPS

[75] Inventors: David T. Green; Richard A. McGarry, both of Norwalk; Graham Smith, Ridgefield, all of Conn.

[73] Assignee: United States Surgical Corporation, Norwalk, Conn.

[21] Appl. No.: 635,262

[22] Filed: Jul. 27, 1984

[51] Int. Cl.$^4$ .................................................. A61B 17/12
[52] U.S. Cl. ................................................... 128/325
[58] Field of Search ................... 128/325, 326, 334 R, 128/334 C; 29/243.56; 72/410

[56] References Cited

U.S. PATENT DOCUMENTS

| | | | |
|---|---|---|---|
| Re. 28,932 | 8/1976 | Noiles | 227/19 |
| 1,199,653 | 9/1916 | Bacolini . | |
| 1,203,269 | 10/1916 | Richter . | |
| 2,090,831 | 8/1937 | Burkhardt | 1/49.1 |
| 2,194,748 | 3/1940 | Glaser | 81/3 |
| 2,237,589 | 4/1941 | Dole | 1/56 |
| 2,594,102 | 4/1952 | Vollmer | 1/49.1 |
| 2,733,441 | 2/1956 | White | 1/49.1 |
| 2,744,251 | 5/1956 | Vollmer | 1/49.1 |
| 2,968,041 | 1/1961 | Skold | 1/49.1 |
| 3,047,874 | 8/1962 | Kelsey | 1/349 |
| 3,086,208 | 4/1963 | Eby | 1/56 |
| 3,110,899 | 11/1963 | Warren | 1/349 |
| 3,152,336 | 10/1964 | Brady | 1/349 |
| 3,234,636 | 2/1966 | Brown | 29/212 |
| 3,518,993 | 7/1970 | Blake | 128/321 |
| 3,646,801 | 3/1972 | Caroli | 72/410 |
| 3,775,826 | 12/1973 | Reed | 29/212 |
| 3,777,538 | 12/1973 | Weatherly | 72/410 |
| 3,780,416 | 12/1973 | Rider | 29/212 |
| 3,873,016 | 3/1975 | Fishbein | 227/83 |
| 3,882,854 | 5/1975 | Hulka | 128/6 |
| 4,027,510 | 6/1977 | Hiltebrandt | 72/37 |
| 4,152,920 | 5/1979 | Green | 72/410 |
| 4,166,466 | 9/1979 | Jarvik | 128/325 |
| 4,196,836 | 4/1980 | Becht | 227/110 |
| 4,202,480 | 5/1980 | Annett | 227/8 |
| 4,204,623 | 5/1980 | Green | 227/19 |
| 4,226,242 | 10/1980 | Jarvik | 128/325 |
| 4,242,902 | 1/1981 | Green | 72/410 |
| 4,246,903 | 1/1981 | Larkin | 128/325 |
| 4,296,751 | 10/1981 | Blake | 128/325 |
| 4,299,224 | 11/1981 | Noiles | 128/325 |
| 4,316,468 | 2/1982 | Klieman | 128/325 |
| 4,325,376 | 4/1982 | Klieman | 128/325 |
| 4,391,402 | 7/1983 | Campbell | 227/121 |
| 4,396,139 | 8/1983 | Hall | 227/19 |
| 4,406,392 | 9/1983 | Campbell | 227/19 |
| 4,412,539 | 11/1983 | Jarvik | 128/325 |
| 4,425,915 | 1/1984 | Ivanov | 128/325 |
| 4,427,008 | 1/1984 | Transue | 128/325 |
| 4,430,997 | 2/1984 | DiGiovanni | 128/326 |
| 4,440,170 | 4/1984 | Golden | 128/325 |
| 4,450,839 | 5/1984 | Transue | 128/325 |
| 4,450,840 | 5/1984 | Mericle | 128/325 |
| 4,452,357 | 6/1984 | Klieman | 206/339 |
| 4,452,376 | 6/1984 | Klieman | 221/198 |
| 4,478,218 | 10/1984 | Mericle | 128/325 |
| 4,480,640 | 11/1984 | Becht | 72/410 X |
| 4,492,232 | 1/1985 | Green | 128/325 |
| 4,500,024 | 2/1985 | Di Giovanni et al. | 128/334 R X |

FOREIGN PATENT DOCUMENTS

| | | |
|---|---|---|
| 1098483 | 2/1983 | Australia . |
| 1098583 | 2/1983 | Australia . |
| 1098683 | 2/1983 | Australia . |
| 01279 | 4/1984 | PCT Int'l Appl. ................. 128/325 |
| 2074030 | 10/1981 | United Kingdom . |
| 2074031 | 10/1981 | United Kingdom . |

Primary Examiner—Michael H. Thaler
Attorney, Agent, or Firm—Thomas R. Bremer

[57] ABSTRACT

Surgical clip applying apparatus in which clips are delivered to a pair of jaws one at a time for closure around body tissue. The squeezing together of a pair of ring handles causes the jaws to move distally relative to the apparatus. The jaws contact a pair of inclined surfaces on the shaft of the apparatus and are thereby forced together, causing the distal-most clip in a linear array to be closed around body tissue. Release of the handles returns the jaws to the original positions so that another clip closing cycle can be initiated. An escapement mechanism interacts with the jaws to ensure that only one clip at a time from the linear array is delivered to the jaws. A clutch assembly ensures that each step in the clip closing and return cycle is completed in the proper sequence.

13 Claims, 31 Drawing Figures

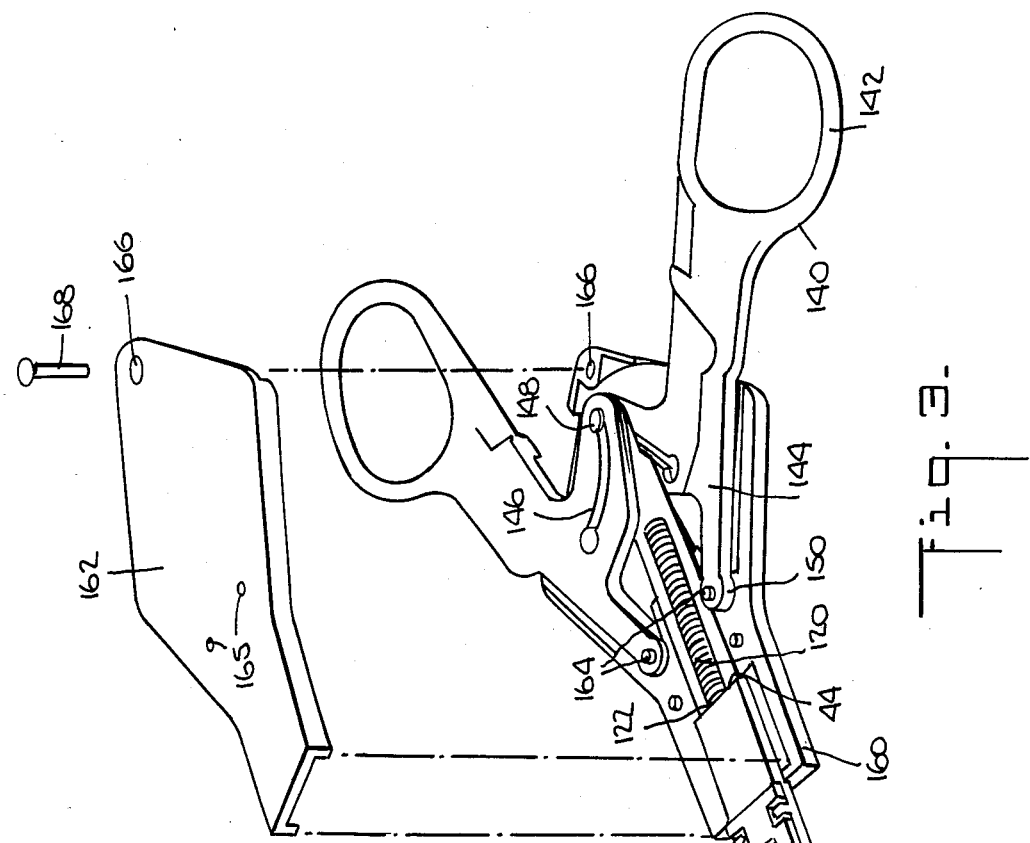
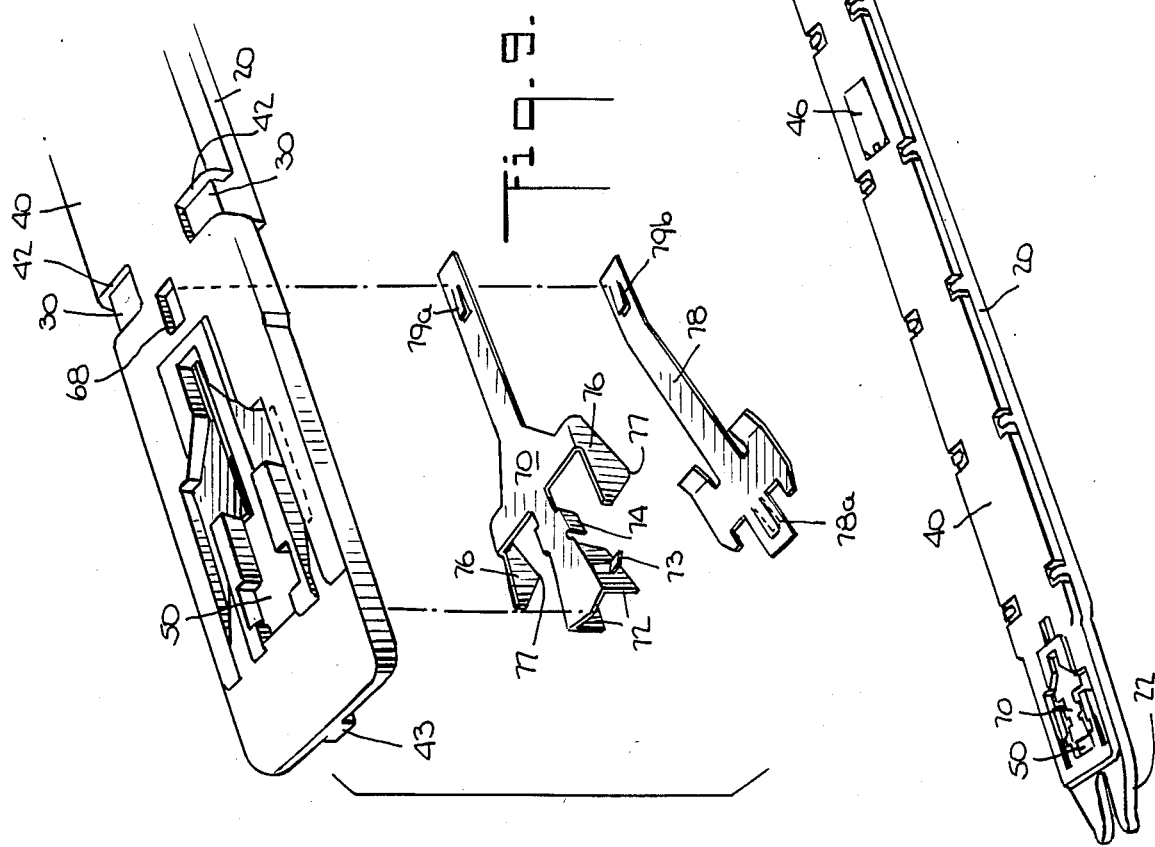

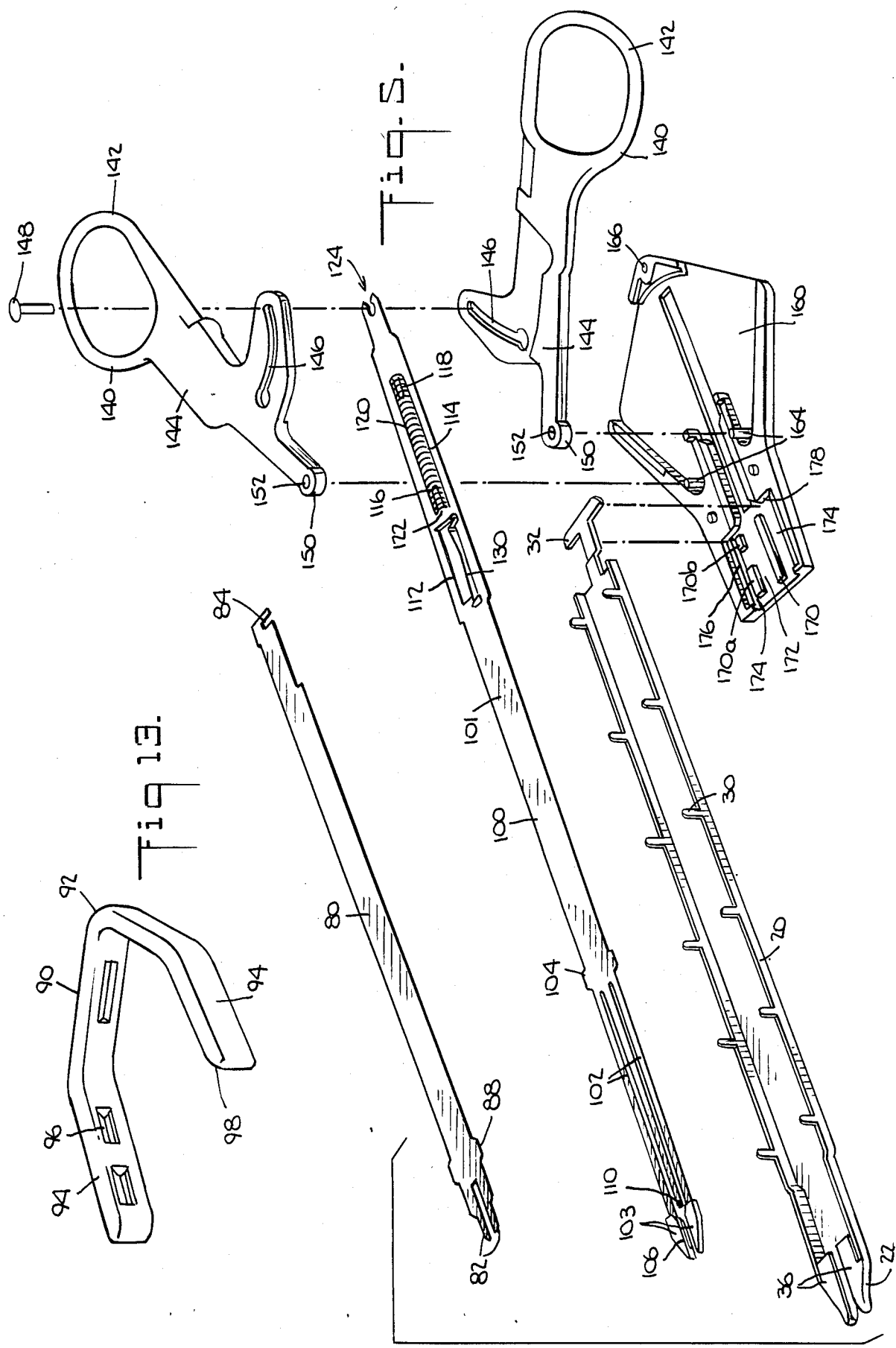

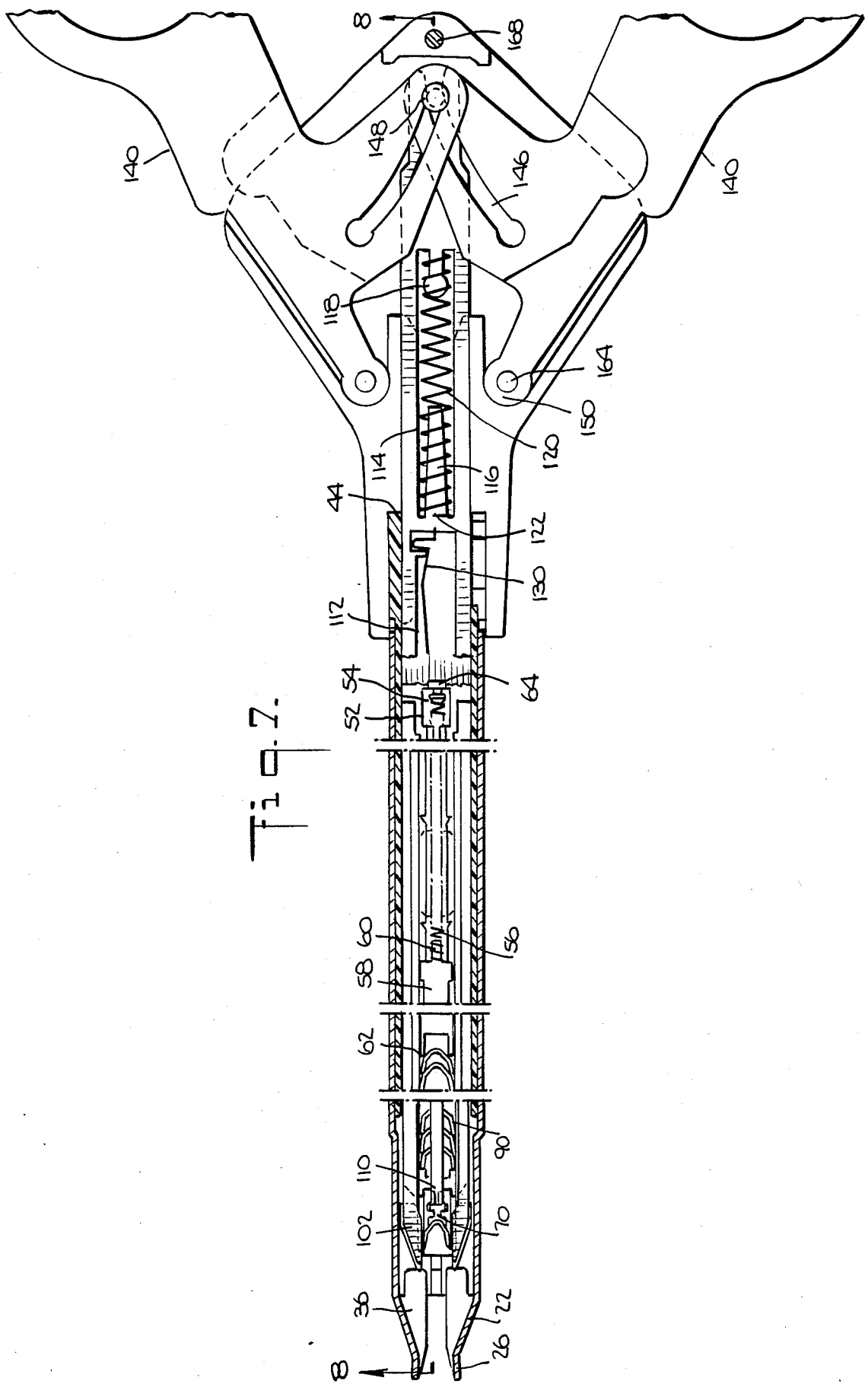

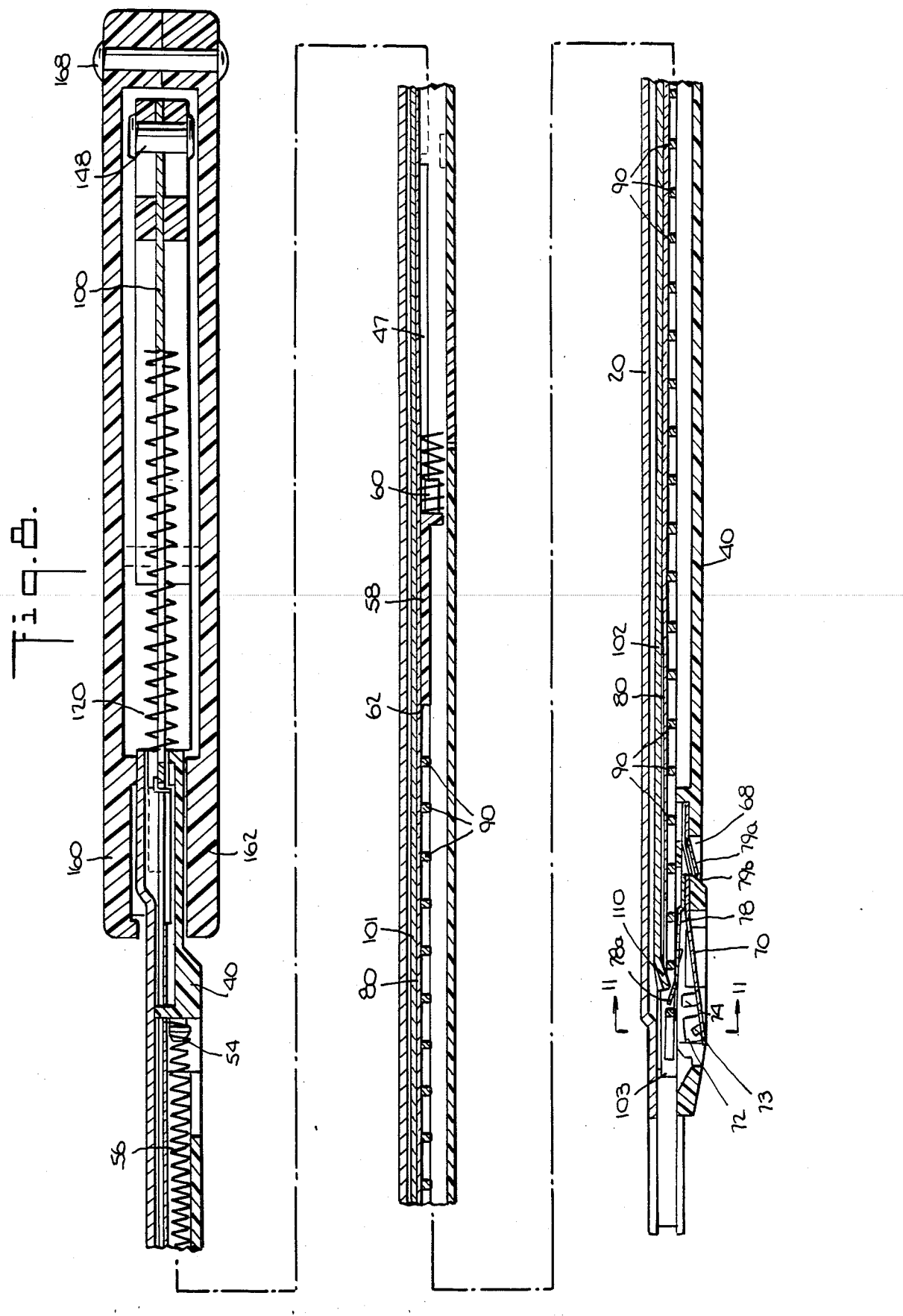

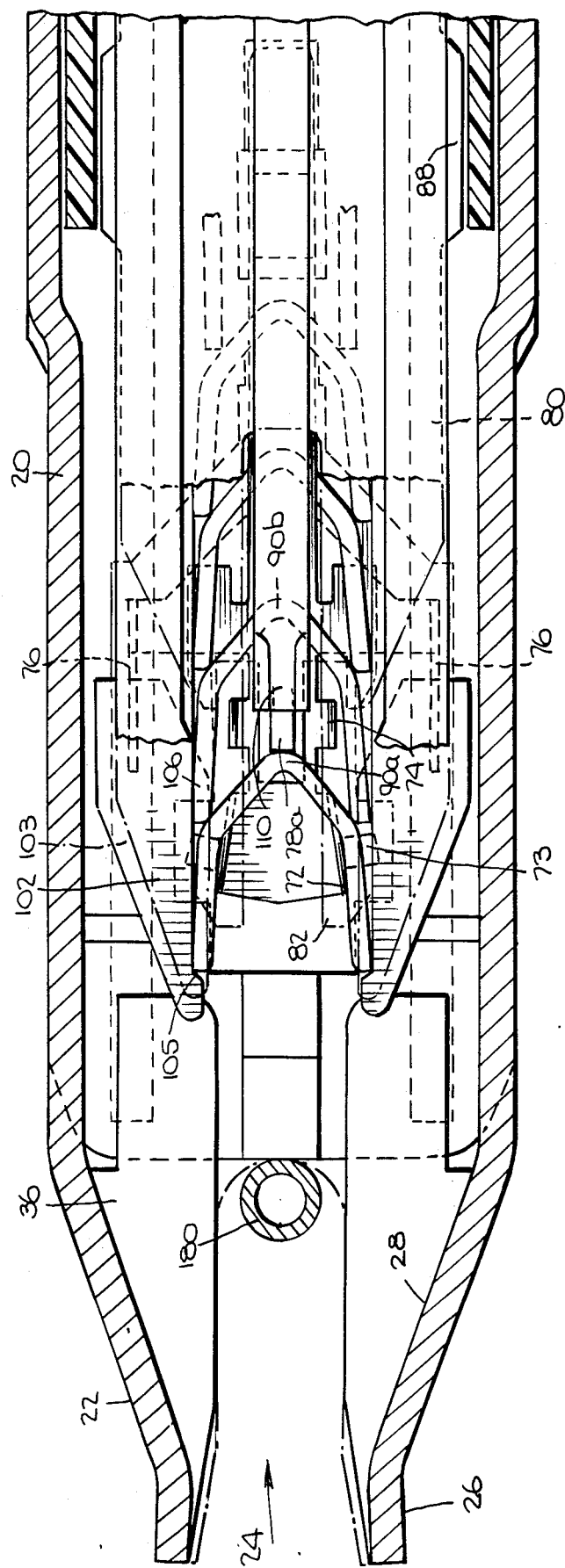

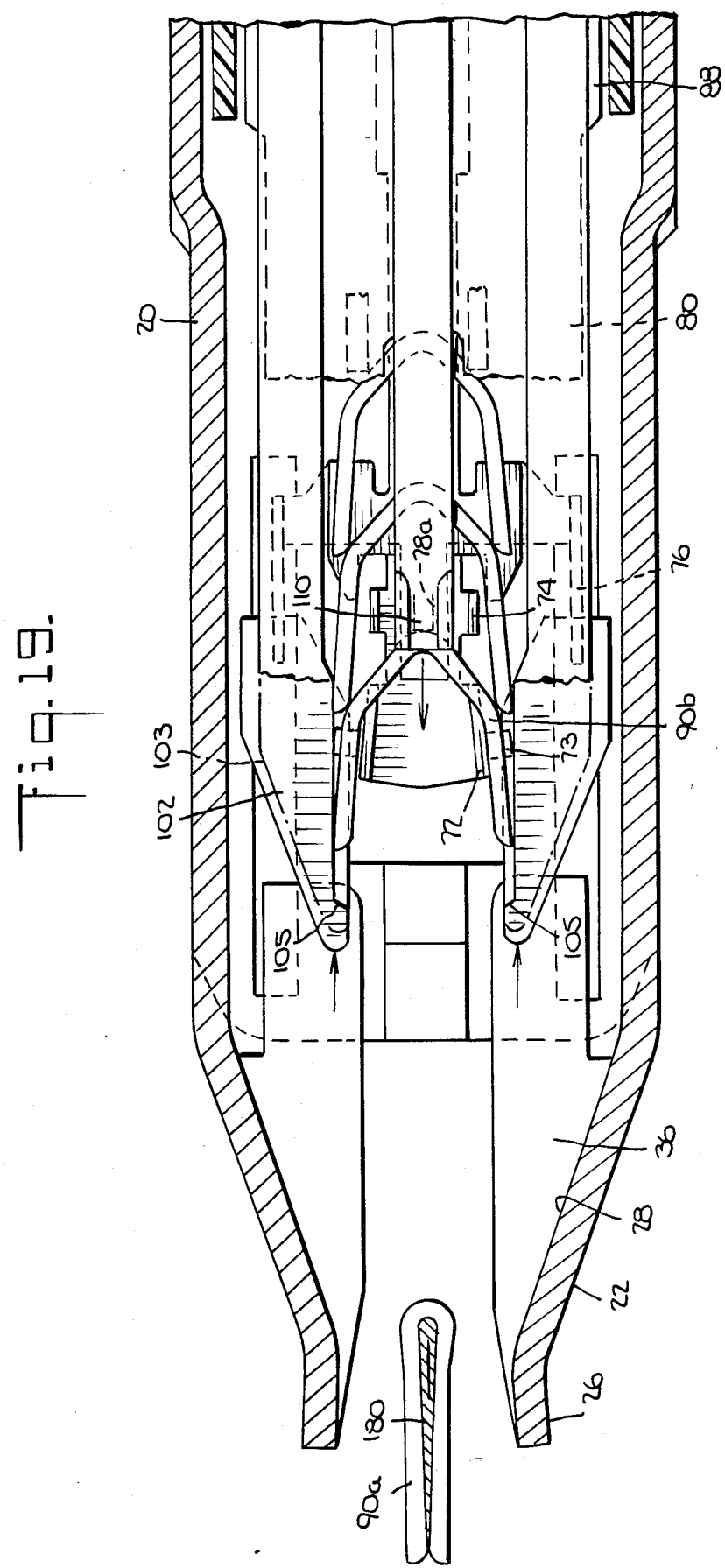

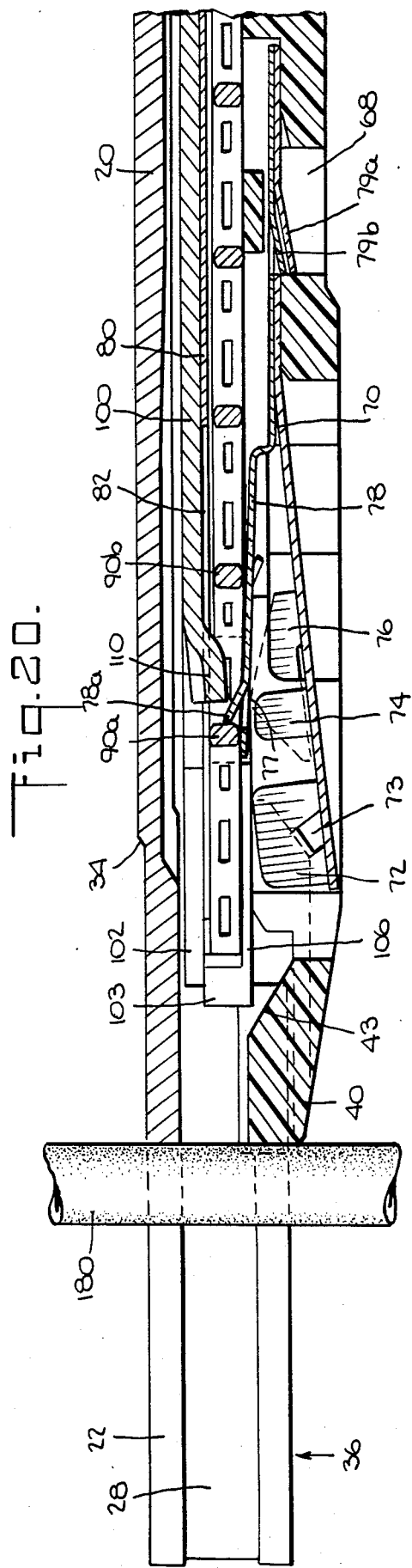
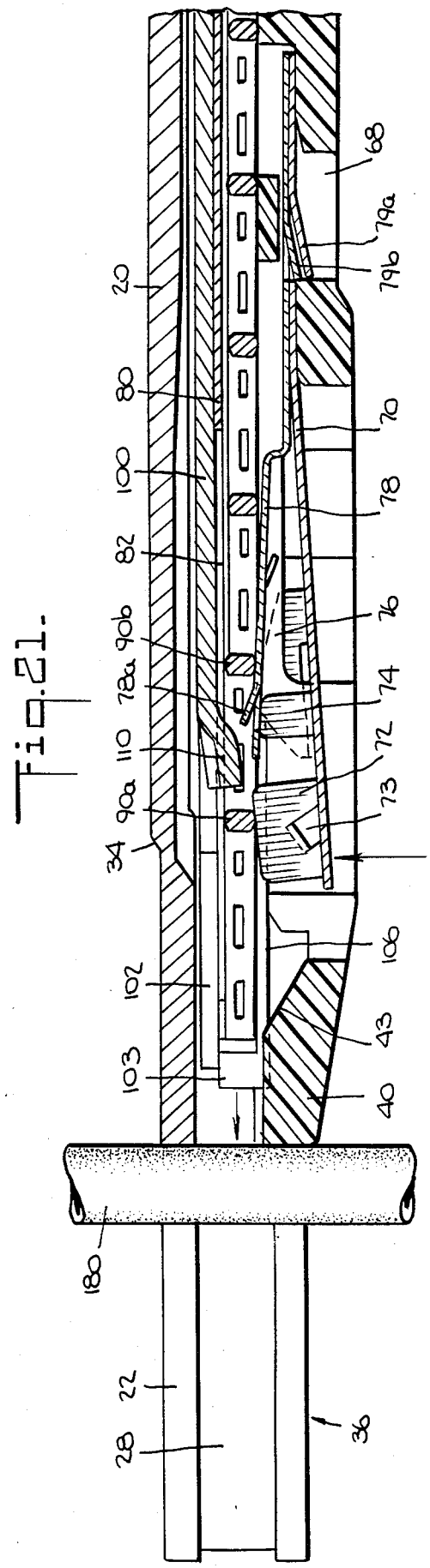

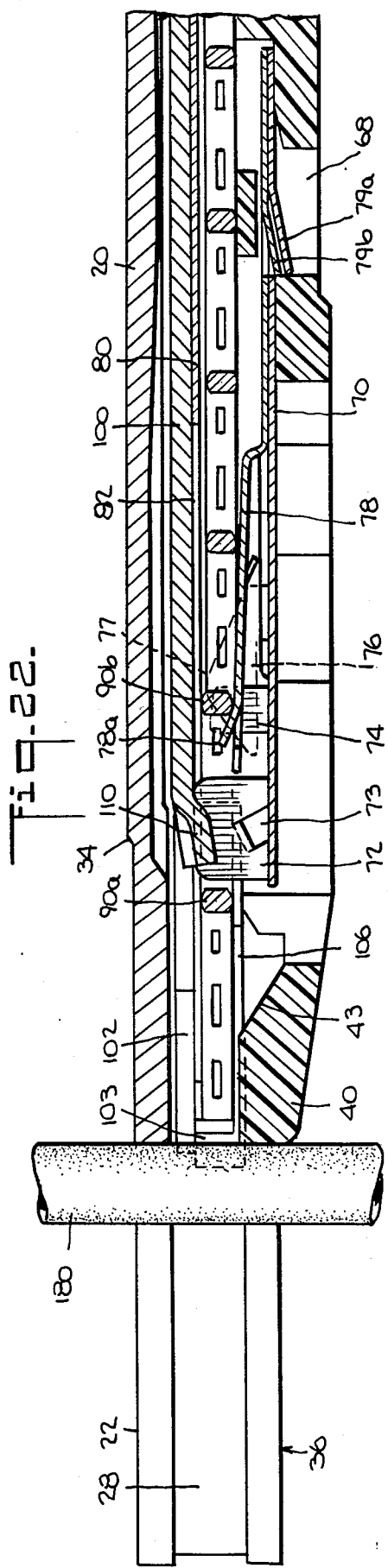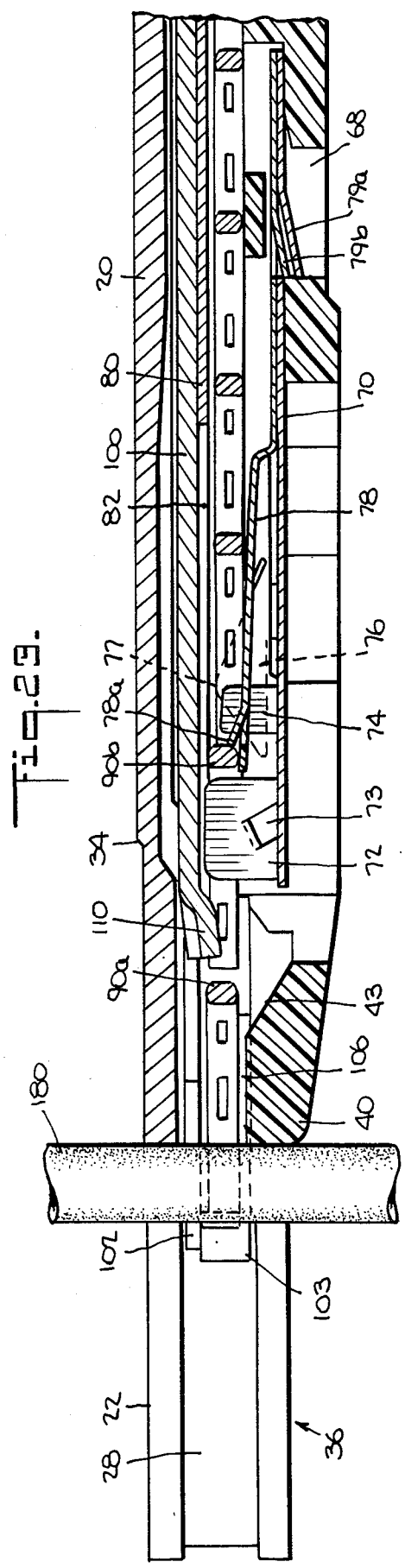

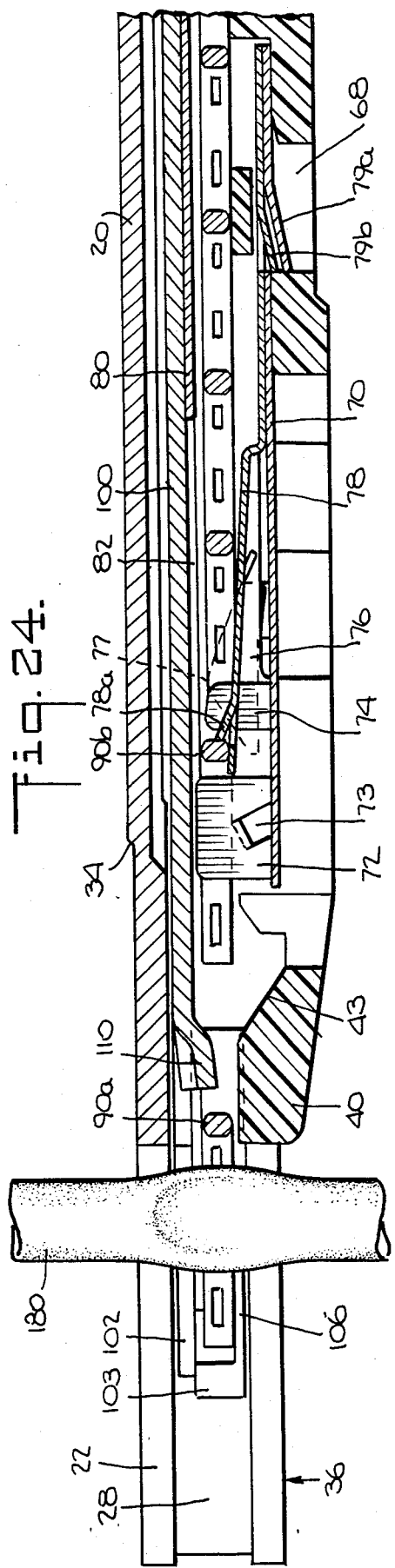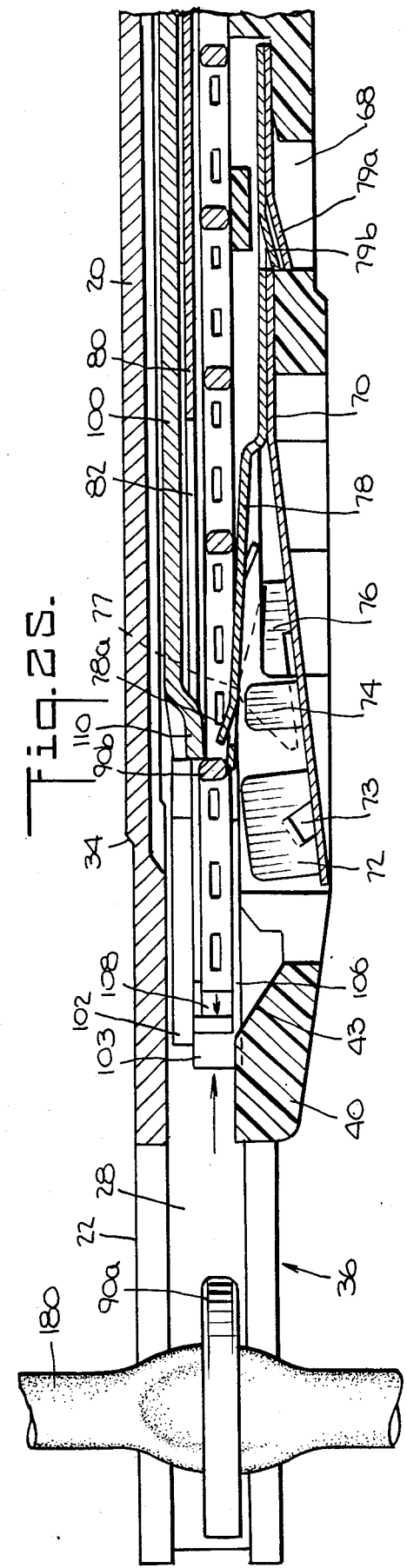

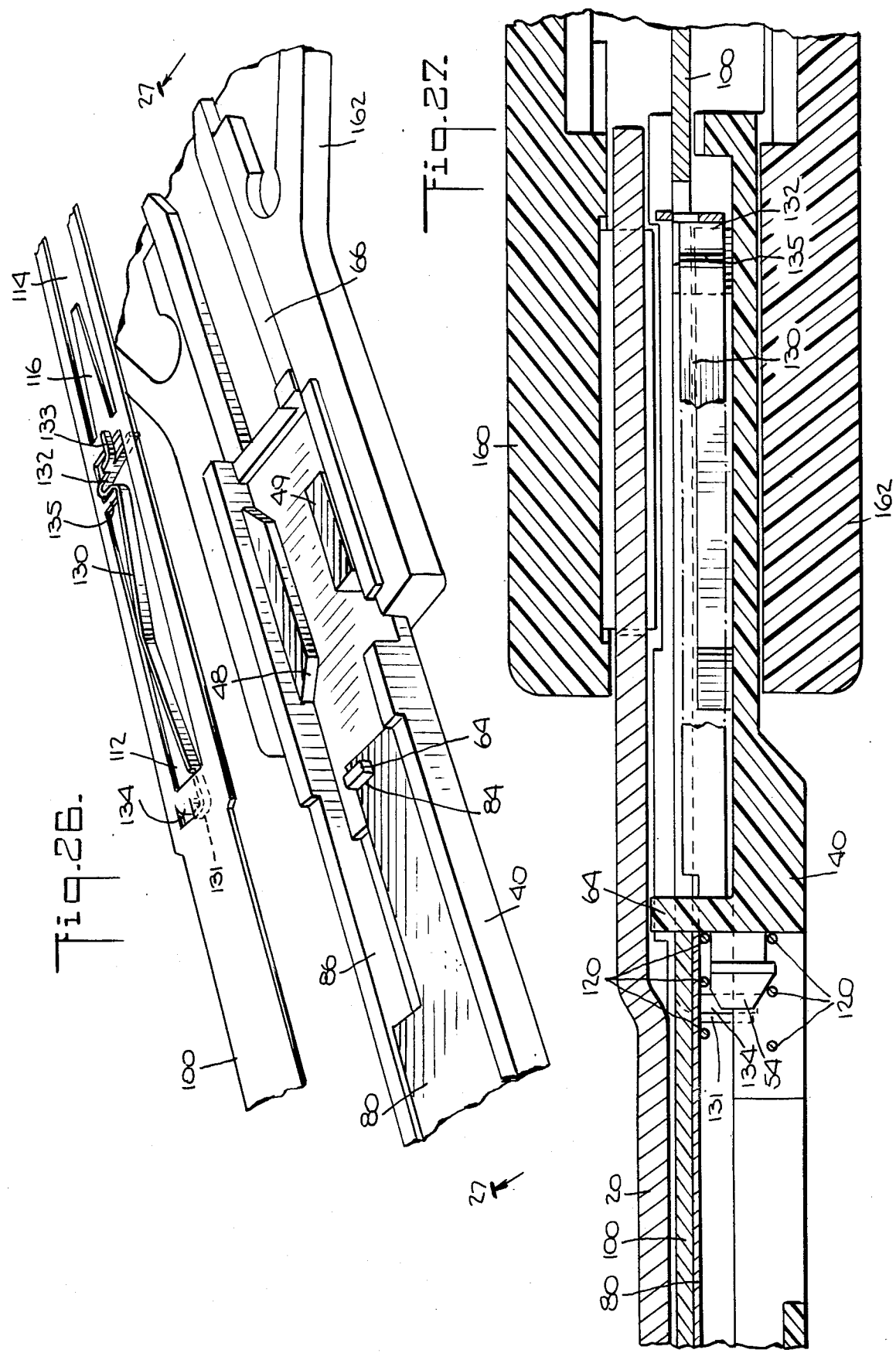

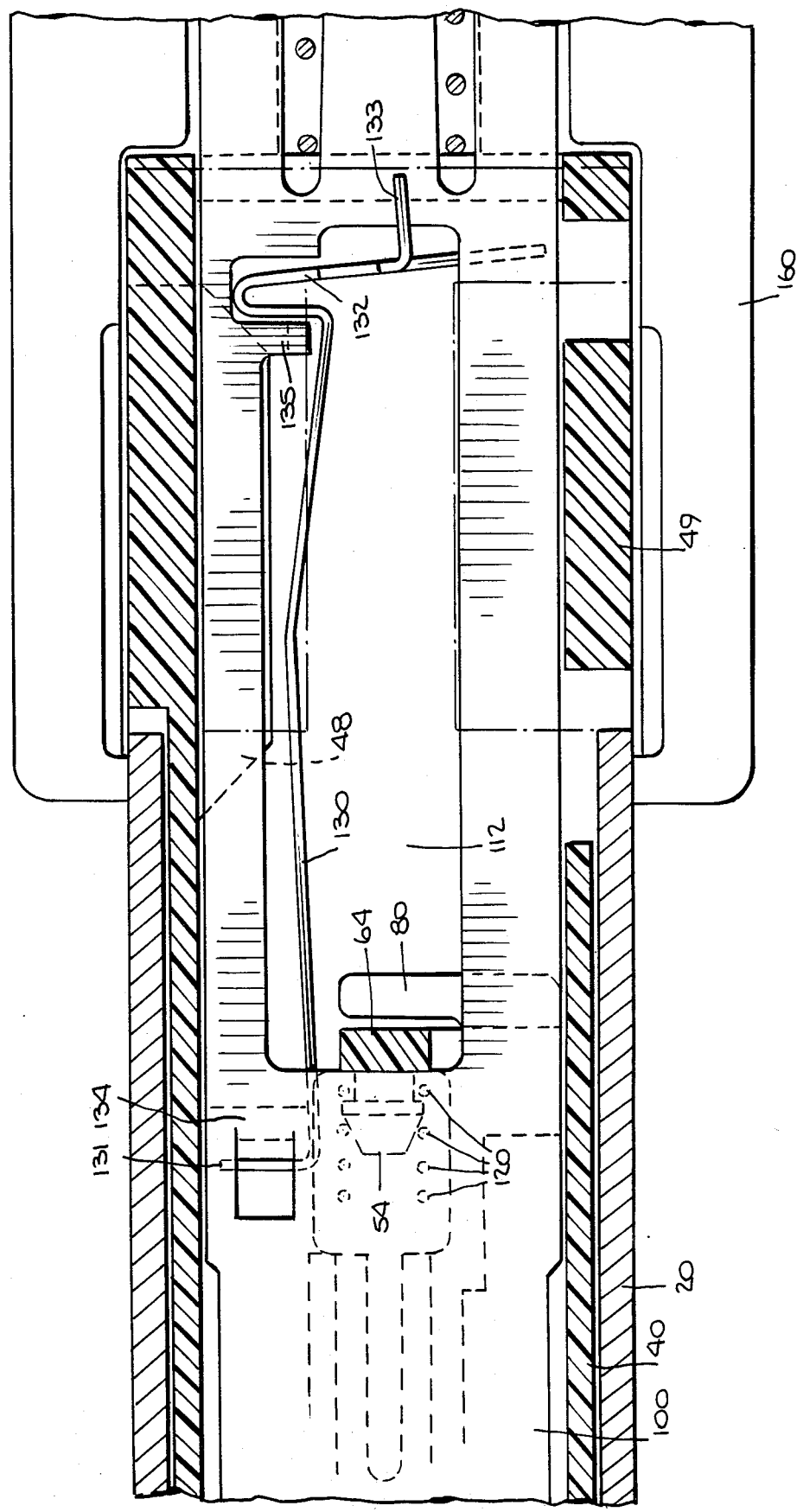

APPARATUS FOR APPLYING SURGICAL CLIPS

BACKGROUND OF THE INVENTION

This invention relates to apparatus for applying surgical clips, especially hemostatic clips, to body tissue such as blood vessels. More particularly, the invention relates to apparatus having a reduced number of movable parts and which is suitable for one-handed operation to apply a plurality of clips in succession.

Surgical clip appliers typically have a pair of laterally spaced, relatively movable jaws for receiving a clip to be applied to body tissue. When clips must be inserted singly within the jaws, repeated loading may be fatiguing to the surgeon. Consequently, it has been preferred to supply a plurality of clips with the clip applier. The provision of a supply of clips for repeated application by the apparatus has typically required complex clip storage and feed mechanisms, which can be bulky and obscure the surgeon's view of the jaws as they are placed in position to apply clips to body tissue. After the jaws receive a clip, the jaws are brought together to close the clip around the tissue. The most cumbersome and unreliable method for bringing the jaws together is the use of direct manual pressure. The surgeon's hand may limit the view of the clip application site and can make the application of a clip difficult in configned working areas of the body. In other methods, the jaws are cammed together by interaction with a shaft or sleeve, usually in association with actuators and complex linkages.

Accordingly, one object of this invention is to improve and simplify surgical clip applying apparatus.

A more particular object of this invention is to provide surgical clip applying apparatus with a reduced number of relatively movable elements for advancing and closing surgical clips.

A further object of this invention is to provide a simplified structure for regulating the sequential delivery of clips to the clip closing jaws of the apparatus.

SUMMARY OF THE INVENTION

These and other objects of the invention are accomplished in accordance with this invention, which provides a clip closing element associated directly with a pair of actuating handles for longitudinal reciprocal motion relative to the clip applier. All other elements are fixed longitudinally. The clip closing element terminates in a pair of jaws which function both to close clips and to assist in the control of the feeding of clips.

The distal-most clip in a linear array of clips is prepositioned within the jaws. Squeezing the pair of actuating handles together directly causes distal, longitudinal motion of the clip closing means without the need for complex linkages. The jaws contact a pair of laterally spaced cam surface portions of a fixed shaft which are inclined toward one another in the distal direction. The cam surface portions force the jaws toward each other to close the distal-most clip around body tissue.

The release of the actuating handles causes longitudinal motion of the jaws in the proximal direction. During this return stroke, the jaws contact an escapement mechanism in the plane of the clip array. The jaws urge the escapement out of the plane of the clps to permit the next clip in the array to enter the jaws. During the ensuing forward stroke, the distal motion of the jaws releases the escapement so that it can return to the plane of the clip array and block the distal motion of the remaining clips in the array.

The two-stage cycle can be repeated until the supply of clips is exhausted. The simple design of the apparatus facilitates its one-handed operation, improves access to and visibility of the clip application site, and economically permits the apparatus to be made disposable.

Further features of the invention, its nature and various advantages will be more apparent from the accompanying drawings and the following detailed description of the invention.

BRIEF DESCRIPTION OF THE DRAWINGS

FIG. 2 is a perspective view of the bottom of the clip applier.

FIGS. 3 through 5 are increasingly exploded perspective views of the clip applier.

FIG. 6 is a cross-section taken along line 6—6 of FIG. 1.

FIG. 7 is a longitudinal section taken along line 7—7 of FIG. 1.

FIG. 8 is a longitudinal section taken along line 8—8 of FIG. 7.

FIG. 9 is a pespective view of an escapement mechanism and the surrounding portion of the clip applier.

FIG. 10 is a split plan view of part of the clip applier with a portion of the bottom track surface cut away. The top portion of FIG. 10 shows a portion of the clip closing means with one attached jaw. The bottom portion of FIG. 10 shows a portion of the escapement mechanism.

FIG. 11 is a cross-section taken along line 11—11 of FIG. 8 with the escapement mechanism cammed out of the plane of an array of clips by a pair of jaws.

FIG. 12 is a view similar to FIG. 11 except that distal motion of the jaws has permitted the escapement mechanism to move into the plane of the array of clips.

FIG. 13 is a perspective view of a surgical clip for use with the clip applier of FIG. 1.

FIG. 14 is an enlarged view of a portion of the apparatus shown in FIG. 7. The clip applier is shown at the initial position of the clip closing cycle.

FIG. 19 is a view similar to FIG. 14 except that retraction from the peak clip closing position to nearly the initial position of the clip closing cycle is shown.

FIG. 20 is an enlarged view of a portion of the apparatus shown in FIG. 8. The clip applier is shown at the initial position of the clip closing cycle.

FIG. 21 is a view similar to FIG. 20 except that a first intermediate clip position is shown.

FIG. 22 is a view similar to FIG. 20 except that a second intermediate clip position is shown.

FIG. 23 is a view similar to FIG. 20 except that a third intermediate clip position is shown.

FIG. 24 is a view similar to FIG. 20 except that a fourth intermediate clip position is shown.

FIG. 25 is a view similar to FIG. 20 except that retraction from the peak clip closing position to nearly the initial position of the clip closing cycle is shown.

FIG. 26 is an exploded perspective view of the clip applier showing a clutch assembly.

FIG. 27 is a longitudinal section taken along line 27—27 of FIG. 26.

FIG. 28 is an enlarged plan view of the clutch assembly in its initial position.

DETAILED DESCRIPTION OF THE INVENTION

Although this invention is also applicable to other embodiments, such as surgical clip appliers which are permanent and can be reused by inserting additional clips after the initial supply is exhausted, the invention will be fully understood from an explanation of its application to clip appliers which are totally disposable after the initial supply of clips is exhausted.

Figure 1:
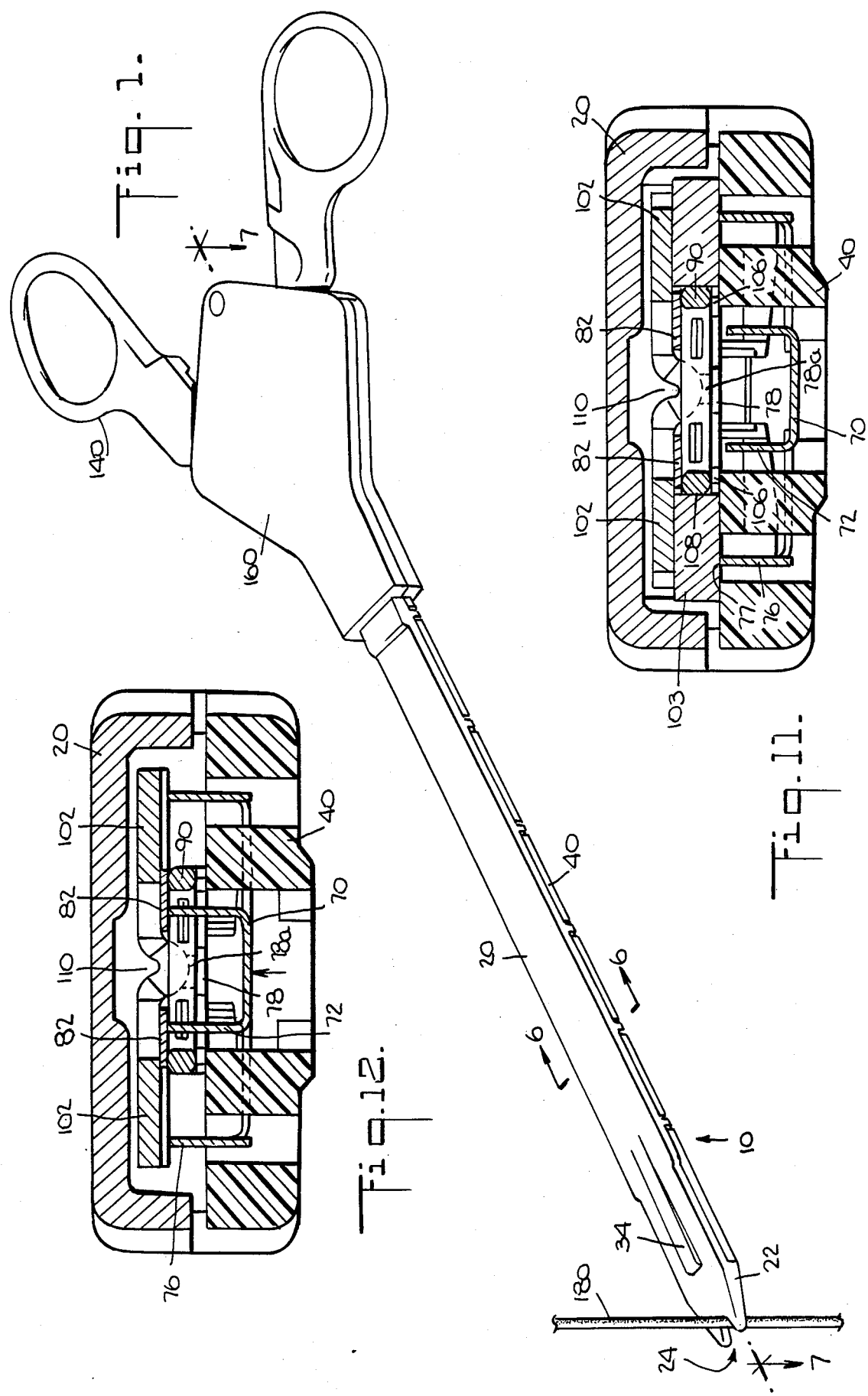
FIG. 1 is a perspective view of the top of a clip applier.
Figures 2, 6, 10:
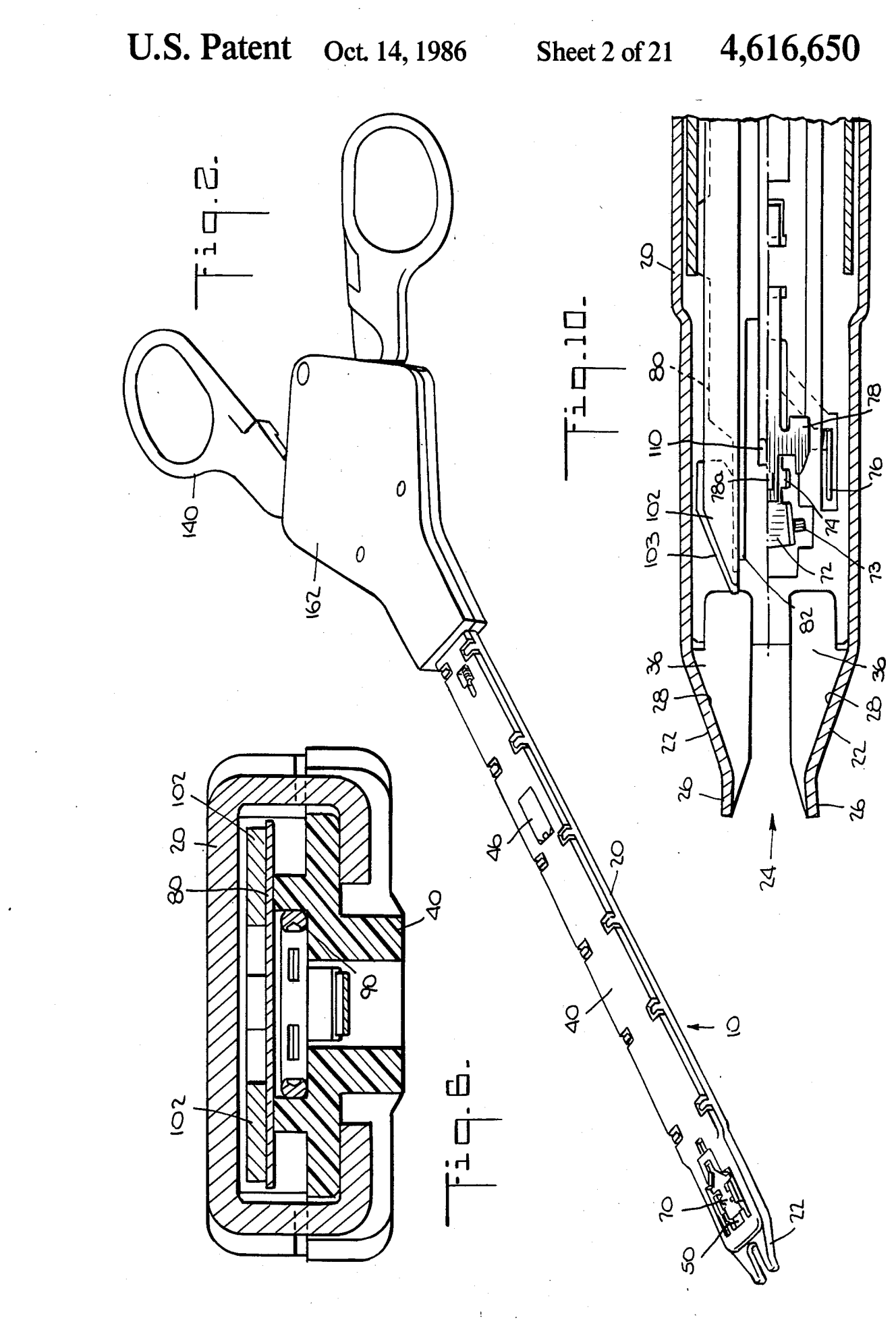

FIGS. 1 and 2 show clip applier 10, which includes a longitudinal shaft 20 having a distal wrap portion 22. Wrap portion 22 has a slot 24 for admitting the body tissue to be clipped. The body tissue will most frequently be a tubular structure such as blood vessel 180. Wrap portion 22 also has a pair of wrap plates 36, which define a passage bordered by cam surfaces 28 (see FIG. 10). Ends 26 of wrap portion 22 may be flared to assist the surgeon in guiding tubular structure 180 into slot 24. Longitudinal shaft 20 is provided with ramp 34 for a purpose to be described below.

Longitudinal shaft 20 is operatively associated with track 40. Referring also to FIG. 9, track 40 is provided with a plurality of pairs of notches 42 and longitudinal shaft 20 is provided with a plurality of pairs of tabs 30 which are bent to fit into the plurality of notches 42 to secure longitudinal shaft 20 to track 40.

The distal portion of track 40 contains opening 50 to receive and retain escapement mechanism 70, which will be described in detail below. The proximal portion of track 40 receives track insert 46.

Longitudinal shaft 20 and track 40 are inserted and retained within the distal portions of top body part 160 and bottom body part 162. A pair of ring handles 140 are inserted and retained within the proximal potions of body parts 160 and 162.

As shown in FIG. 3, body parts 160 and 162 are each provided in their proximal portions with an aperture 166. Rivet 168 is passed through apertures 166 to help hold together the proximal portions of body parts 160 and 162. Projections 164 of body part 160 are inserted in apertures 165 of body part 162. Conventional means, such as an adhesive, are applied to hold together the other abutting surfaces of body parts 160 and 162.

Figure 4:
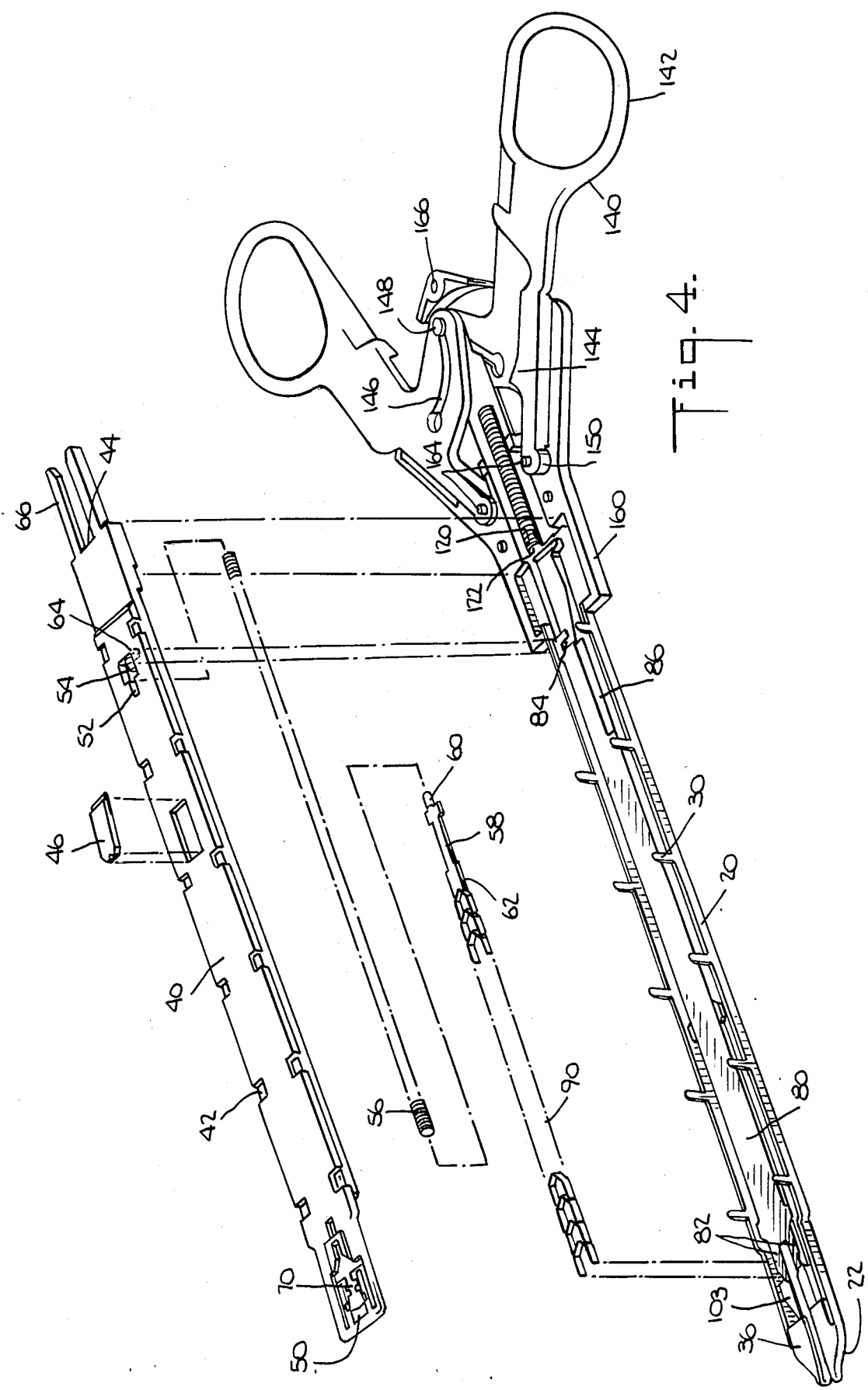

FIG. 4 shows a number of the elements retained within the assembly of longitudinal shaft 20 and track 40. The proximal end of track 40 has an opening 52 with a distally projecting prong 54, which is fitted into the proximal end of compressible spring 56 (see also FIG. 7). The distal end of spring 56 is fitted into the proximal end 60 of clip follower 58. This distal end of spring 56 and clip follower 58 reciprocate within longitudinal channel 47 on the underside of track 40 (shown in FIG. 8). Distal surface 62 of clip follower 58 contacts the rearmost clip 90 in a linear array.

Linear clip array 90 is confined within track 40 and clip cover 80. The distal end of clip cover 80 terminates in a pair of tines 82. Prong 64 projecting downwardly from track 40 fits into notch 84 in clip cover 80. This connection renders clip cover 80 stationary with respect to track 40. Prong 64 also contacts the forward end of channel 112 of clip closing means 100 (shown in FIG. 5) to stop rearward motion of clip closing means 100. Cut-out 86 in the proximal portion of clip cover 80 provides clearance for the motion of the clutch assembly to be described below.

During assembly of the clip applier, clips 90, clip follower 58, and spring 56 are inserted through an opening created by removal of track insert 46. One end of spring 56 is fitted to prong 54 at track opening 52. Track insert 46 is then re-attached to track 40 by conventional means (e.g., snap fit).

Track 40 has two rearwardly-projecting prongs 66, which fit within a recess (not shown in FIG. 4) on the underside of body part 162.

FIG. 5 shows the remaining elements retained within the assembly of longitudinal shaft 20 and track 40. Clip closing means 100 comprises member 101 and two laterally spaced arms 102 extending from member 101. Each arm 102 terminates in a jaw 103. Clip stop 110 also extends from member 101 and is located between arms 102.

Clip cover 80 lies between arms 102 of clip closing means 100 and the array of clips 90 (alos see FIG. 6). However, jaws 103 on arms 102 extend beneath the plane of the tines 82 of clip cover 80 to contact distalmost clip 90a (shown in FIG. 11). Tines 82 assist the entry of a clip into the jaws 103.

A pair of oppositely spaced projecting surfaces 104 aid in fitting clip closing means 100 within longitudinal shaft 20 and track 40 and enable clip closing means 100 to be narrower throughout most of its length than if projecting surfaces 104 were not used. A similar function is performed by oppositely spaced projecting surfaces 88 on clip cover 80.

The rear portion of clip closing means 100 contains openings 112 and 114. Opening 112 accommodates clutch spring 130. Opening 114 has opposing prongs 116 and 118 onto which spring 120 is positioned. Forward end 122 of spring 120 is in constant contact with the rear surface 44 of track 40 (see FIG. 3).

The rear portion of longitudinal shaft 20 has a fit element 32 for insertion into body part 160. Body part 160 has projection 170, which is parallel to spaced projections 170a and 170b. Projections 170 and 170a,b, define the sides of trough bed 172. Slots 174 are located between projection 170 and side wall 176 on one side and between projections 170a,b and side wall 176 on the other. Fit element 32 fits into trough bed 172, is confined by rear wall 178 of body part 160, and extends into the rear portions of slots 174.

Body part 160 includes a pair of projections 164 for retaining ring handles 140. Each ring handle 140 has a finger ring 142 and a shank 144. Shank 144 terminates in knob 150, which has an aperture 152. Each ring handle 140 is fitted to body part 160 by placing each aperture 152 onto its respective projection 164.

Each shank 144 also has a slot 146. When ring handles 140 are fitted to body part 150, slots 146 will partially overlap. Different portions of slots 146 will overlap throughout the clip application cycle, during which ring handles 140 are squeezed toward each other and then are returned to their original separated position.

Recess 124 is provided in the rearmost part of clip closing means 100. Recess 124 lies between slots 146 of ring handles 140, and pin 148 passes through the slots and the recess, thereby providing a direct linkage between ring handles 140 and clip closing means 100.

The assembly of the complete clip applier may be summarized as follows. Referring to FIGS. 1-8, clip closing means 100 is placed within longitudinal shaft 20. Clip cover 80 is attached to track 40 and then is placed atop clip closing means 100 so that proximal surface 44 of track 40 contacts, but does not compress, spring 120 of clip closing means 100. Track 40 and longitudinal shaft 20 are attached to each other by fitting tabs 30 into slots 42. This creates a subassembly of longitudinal shaft 20, clip closing means 100, clip cover 80, and track 40, of which only clip closing means 100 is movable longitudinally.

Clip closing means 100 and ring handles 140 are then linked by pin 148. Apertures 152 of ring handles 140 and fit element 32 of longitudinal shaft 20 are then fitted into projections 164 and trough bed 172, respectively, of top body part 160. Bottom body part 162 is attached by passing projections 164 through apertures 165 and placing prongs 66 of track 40 within the recess of bottom body part 162. Top and bottom body parts 160 and 162 are the connected by passing rivet 168 through apertures 166. Track insert 46 is removed from track 40 to enable clips 90, clip follower 58, and spring 56 to be inserted. Track insert 46 is then repositioned to complete the assembly.

The clip applier as shown in the drawings is substantially planar. However, in one embodiment of the invention (not shown in the drawings), the distal portion of the clip applier has an arcuate shape (that is, the left end of the device in FIG. 1 is curved downward) to provide better visibility of the operative site for the surgeon during the application of clips. In the preferred embodiment, the distal portion of longitudinal shaft 20 is permanently arced, and clip closing means 100, clip cover 80, and track 40 are produced as substantially planar elements, but are sufficiently flexible to conform to the arcuate shape of shaft 20. Preferably, longitudinal shaft 20, clip closing means 100, and clip cover 80 are made of stainless steel, and the track 40 is made of plastic (e.g., LEXAN ® polycarbonate resin).

In another preferred embodiment of this invention (not shown in the drawings), a method for indicating the number of clips remaining in the clip applier is provided. Track 40 is transparent plastic and has numbered lines corresponding to the positions of clips 90 in the linear array. A colored dot is placed on the surface of clip follower 58 behind the proximal-most clip in the linear array. The surgeon observes the colored dot in alignment with a numbered line and thereby ascertains the number of clips remaining in the clip applier. The disposable clip applier is discarded when no clips remain.

FIG. 9 shows escapement 70 and opening 50 in the distal portion of track 40 which receives escapement 70. Escapement 70 is preferably made of stainless steel and includes three pairs of oppositely spaced projecting surfaces which extend outward and then downward from the axis of the escapement 70. Each of the forwardmost pair of projections 72 has a finger 73, which projects outwardly from the vertical portion of the projecting surface. The rearmost pair of projections 76 extends beyond the middle pair of projections 74 in both the lateral and longitudinal directions. In the assembled clip applier, a lift spring 78 is proximal to the three pairs of projecting surfaces and also extends downwardly. Lift spring 78 has a tab 78a. The rear portions of escapement 70 and lift spring 78 have ears 79a and 79b, respectively, both of which extend to seat in recess 68 of track 40, thereby positioning escapement 70 in track 40 (see also FIG. 20).

FIGS. 8, 10, and 11 show the relative positions of escapement 70, jaws 103, and clip cover tines 82 prior to the squeezing together of ring handles 104. Jaws 103 are in a different plane than escapement 70. As described below, during operation each jaw 103 contacts apex 77 of one of the rearmost pair of projecting surfaces 76 of escapement 70 and cams surface 76 in th direction of track 40 and out of the plane of clip array 90.

FIG. 10 also shows certain features of the distal wrap portion 22 of longitudinal shaft 20. Two wrap plates 36 project inwardly from opposing bottom surfaces of wrap portion 22 (see also FIG. 4). The space between wrap plates 36 and the remainder of wrap portion 22 defines a passage for distal motion of jaws 103. The sides of this passage comprise two laterally spaced cam surfaces 28 which are inclined toward one another in the distal direction. Distal motion of jaws 103 between wrap portion 22 and wrap plates 36 causes them to contact and traverse cam surfaces 28 so that the jaws 103 are forced toward each other to close clip 90 held in the jaws 103. At all times, jaws 103 are confined between wrap portion 22 and wrap plates 36. Thus, jaws 103 can travel only longitudinally within the defined passage.

The distal ends of wrap portion 22 terminate in flared surfaces 26 to provide a wider entry area in slot 24 for admitting the tubular structure 180 (see FIG. 1). That allows for better control of where the clip will be applied. The surgeon first places the walls of slot 24 around tubular structure 180 to provide an approximate positioning. The squeezing of ring handles 140 then automatically moves jaws 103 and distal most clip 90 forward, precisely around tubular structure 180. Thus, there is no need for the surgeon to perform this precise positioning manually. This results in greater speed and accuracy of clip application.

FIG. 11 shows a cross-section of clip applier 10 prior to the squeezing together of ring handles 140. Escapement 70 is shown cammed down, out of the plane of clips 90, by jaws 103. Distal-most clip 90 is separated by clip cover tines 82 from arms 102. However, jaws 103 extend downwardly from arms 102 to contact clip 90. Step 106 on each jaw 103, together with the respective arm 102, define groove 108 that supports one of the clip legs 94.

In FIG. 12, ring handles 140 have been squeezed. Jaws 103 have moved distally carrying clip 90 forward and no longer are in contact with apexes 77 of projections 76. This enables escapement 70 to move up into the plane of the array of clips 90 and thus to block distal motion by all the clips behind the forwardmost one.

FIG. 13 illustrates a clip that may be used with clip applier 10. Clip 90 is preferably made of metal, such as stainless steel, although the use of plastics or other polymers is possible. Clip 90 has a crown 92 and two legs 94.

Crow 92 is that part of clip 90 that is farthest from the ends of clip legs 94. Legs 94 are bent inward to aid in stacking clips in a linear array and to ensure safe closure around a tubular structure. Each clip in the array is in contact with the immediately adjacent clips in the array, with the ends of legs 94 of each clip touching the mid-region of the legs of the clip just ahead of it. The inner surfaces of clips 90 have grooves 96 to assist the clips in gripping body tissue during closure of the clips. The front inner surfaces 98 of clip legs 94 are rounded for safety. The wire used for clips 90 is of generally rectangular cross-section, although different cross-sections may be used as long as they enable the clips to be advanced and closed properly. Various other clip features known to those skilled in the art may be added provided they do not impair operation of the clip appliers of this invention. For example, the clip crown may be curved instead of angular.

The operation of clip applier 10 in carrying out a complete clip closing and return stroke cycle will now be described with reference to FIGS. 14–25. FIGS. 14 and 20 are different views showing the position of the distal end of the clip applier prior to the squeezing together of the ring handles 140. The clip applier is positioned so that tubular structure 180 is within slot 24 of wrap section 22 of longitudinal shaft 20. In the embodiment shown, the clip applier is supplied to the surgeon with the distal-most clip 90a pre-positioned within jaws 103 ready to be closed around tubular structure 180. Alternatively, the surgeon may squeeze and release ring handles 140 to position distal-most clip 90 within jaws 103.

Each jaw 103 is in contact with an apex 77 of the respective rearmost pair of projecting surfaces 76 of escapement 70. In this position, surfaces 76 have been cammed by jaws 103 downward in FIG. 20 so that the forwardmost and middle pairs of projecting surfaces 72 and 74 are out of the plane of the linear array of clips 90.

In FIG. 21, the squeezing of the ring handles has begun. The squeezing together of ring handles 140 causes pin 148 (see FIG. 8) to move forward. Because pin 148 is linked directly to clip closing means 100 at recess 124, squeezing of ring handles 140 also causes clip closing means 100 to move forward with respect to longitudinal shaft 20, track 40, and clip cover 80. In FIG. 21, clip closing means 100 has moved sufficiently in the distal direction so that jaws 103 are no longer in contact with the apexes 77 of projections 76. As a result, escapement 70 has begun to move up into the plane of clip array 90.

Figure 15:
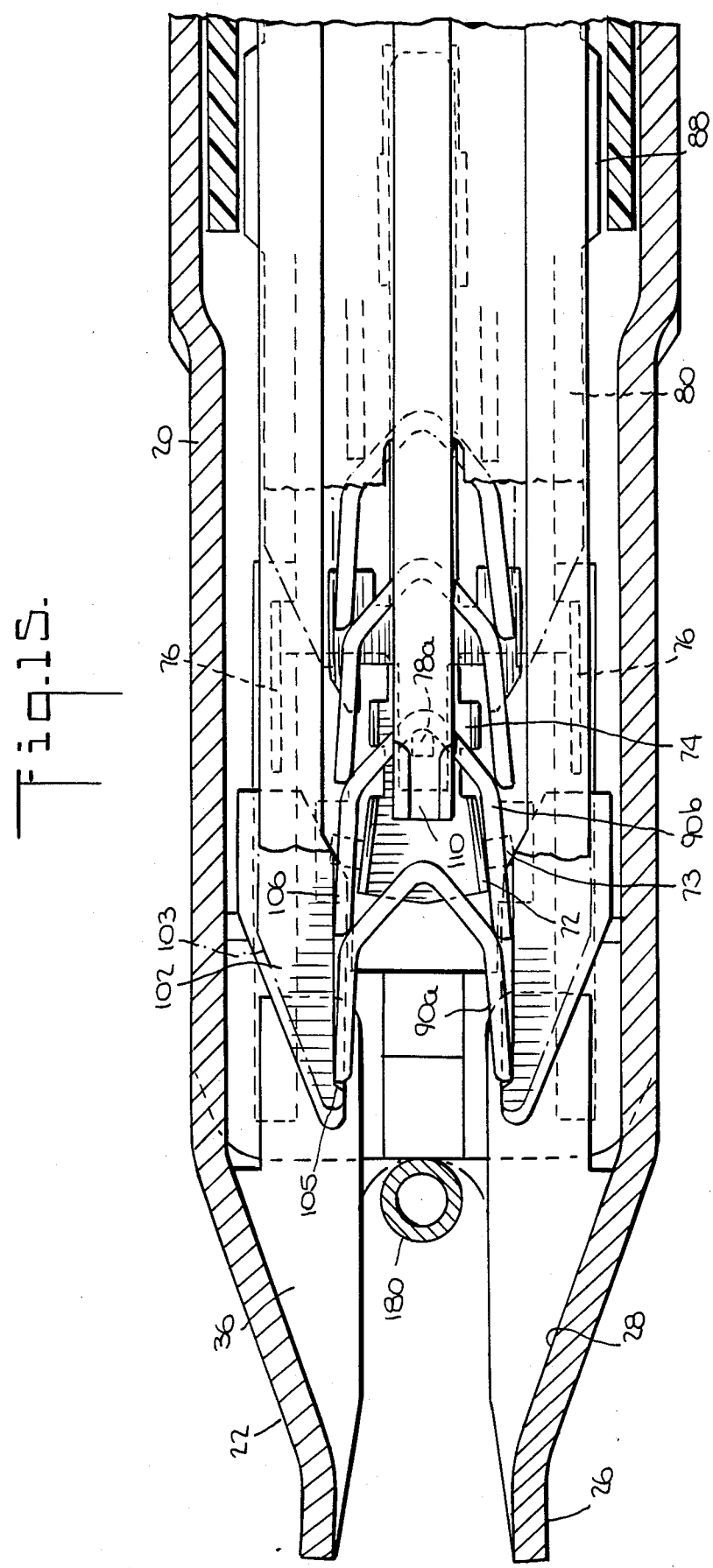
FIG. 15 is a view similar to FIG. 14 except that a first intermediate clip position is shown.

In FIG. 15, clip closing means 100 has continued to move in the distal direction so that forwardmost and middle pairs of projections 72 and 74 have moved into the plane of clip array 90. Portions of legs 94 of clip 90b are then confined between pairs of projections 72 and 74 and maintained in the plane of clips 90 by fingers 73 on projections 72. This blocks further distal motion of the remaining clips in the linear array and ensures that only one clip at a time can enter jaws 103. This also prevents distal motion by spring 56 and clip follower 58.

In FIG. 22, there has been a small amount of additional distal motion by the jaws. Distal-most clip 90a no longer contacts clip 90b.

In FIG. 23, jaws 103 and distal-most clip 90a have begun to surround tubular structure 180. Jaws 103 are not yet in contact with cam surfaces 28 of longitudinal shaft 20.

Figure 16:
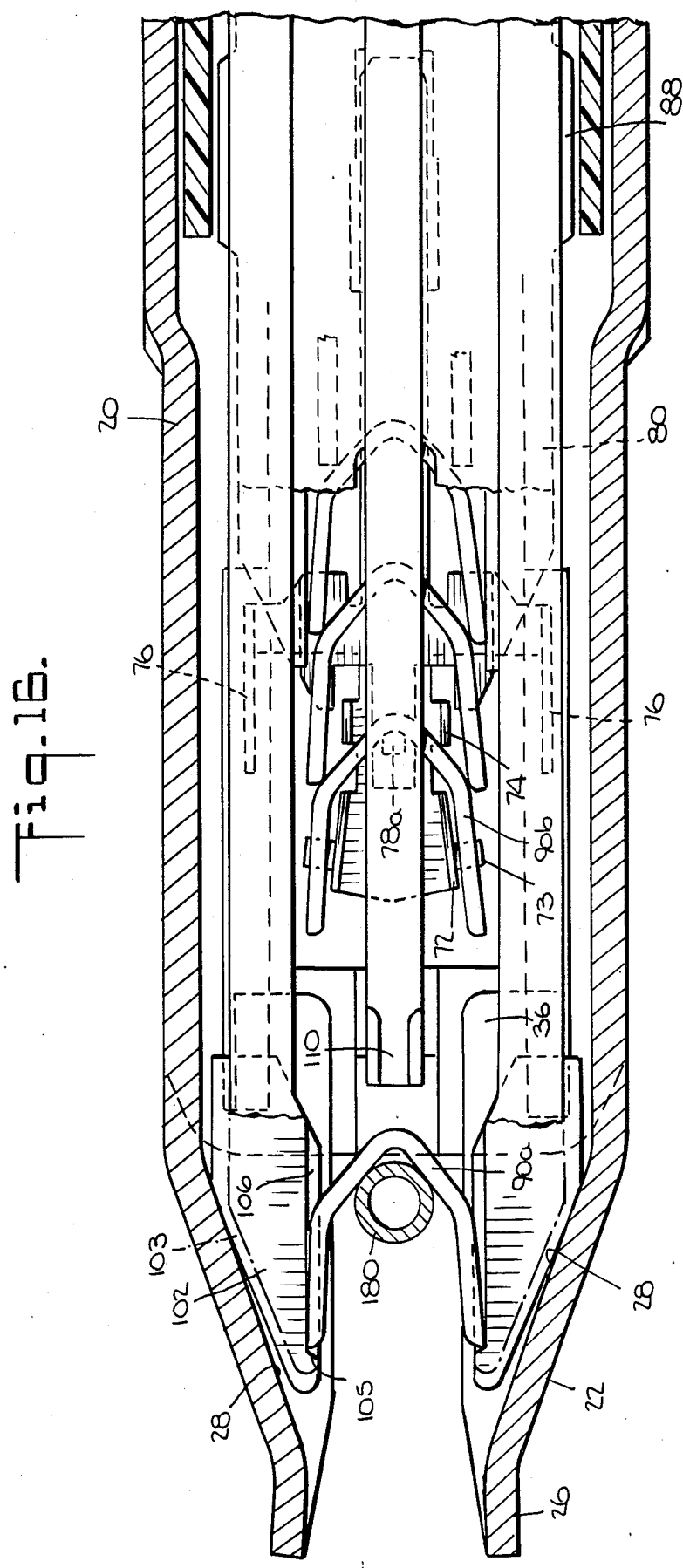
FIG. 16 is a view similar to FIG. 14 except that a second intermediate clip position is shown.

In FIG. 16, jaws 103 have just started to contact cam surfaces 28. Jaws 103 and distal-most clip 90a now surround tubular structure 180.

Figure 17:
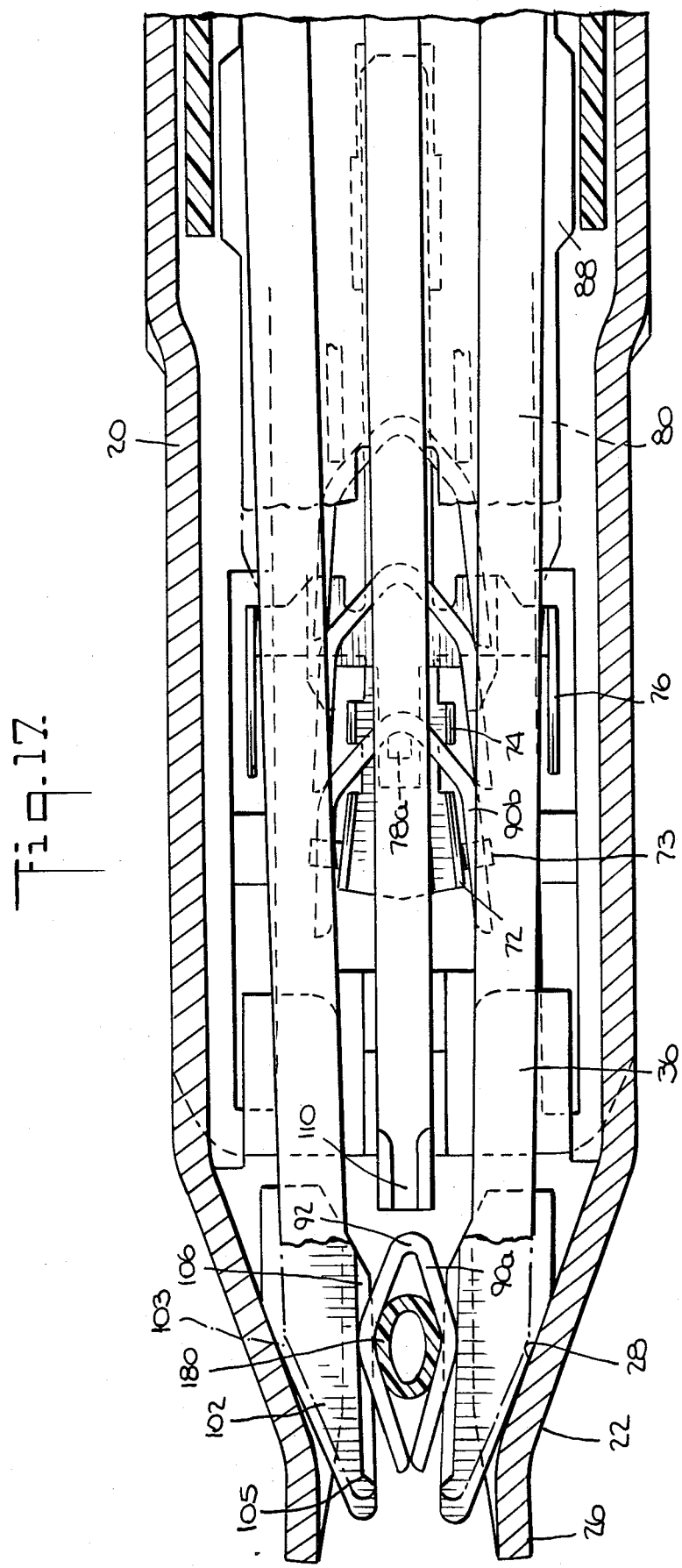
FIG. 17 is a view similar to FIG. 14 except that a third intermediate clip position is shown.

In FIGS. 17 and 24, jaws 103 are being forced toward each other as they move along cam surfaces 28. This causes distal-most clip 90a to close around tubular structure 180. The tips of the clip legs are brought together before other portions of the clip to trap tubular structure 180 within clip 90a. The distal motion of jaws 103 tends to force tubular structure 180 towards clip crown 92 and away from the tips of clip legs 94. This action, along with the use of rounded front inner surfaces 98 of clip legs 94, ensures that the tissue is fully engaged by the clip legs, as is intended. Clip stop 110 prevents any significant proximal motion of clip 90a and thus serves to ensure that clip 90a will be confined within jaws 103 so that it may be closed. Clip stop 110 moves toward the plane of clips as it moves distally. Bevelled block 43 of track 40 (see FIG. 9) maintains clip stop 110 in the plane of clips. Ramp 34 of longitudinal shaft 20 provides clearance for clip stop 110 when clip closing means 100 is in the proximal portion of its reciprocal longitudinal motion.

Figure 18:
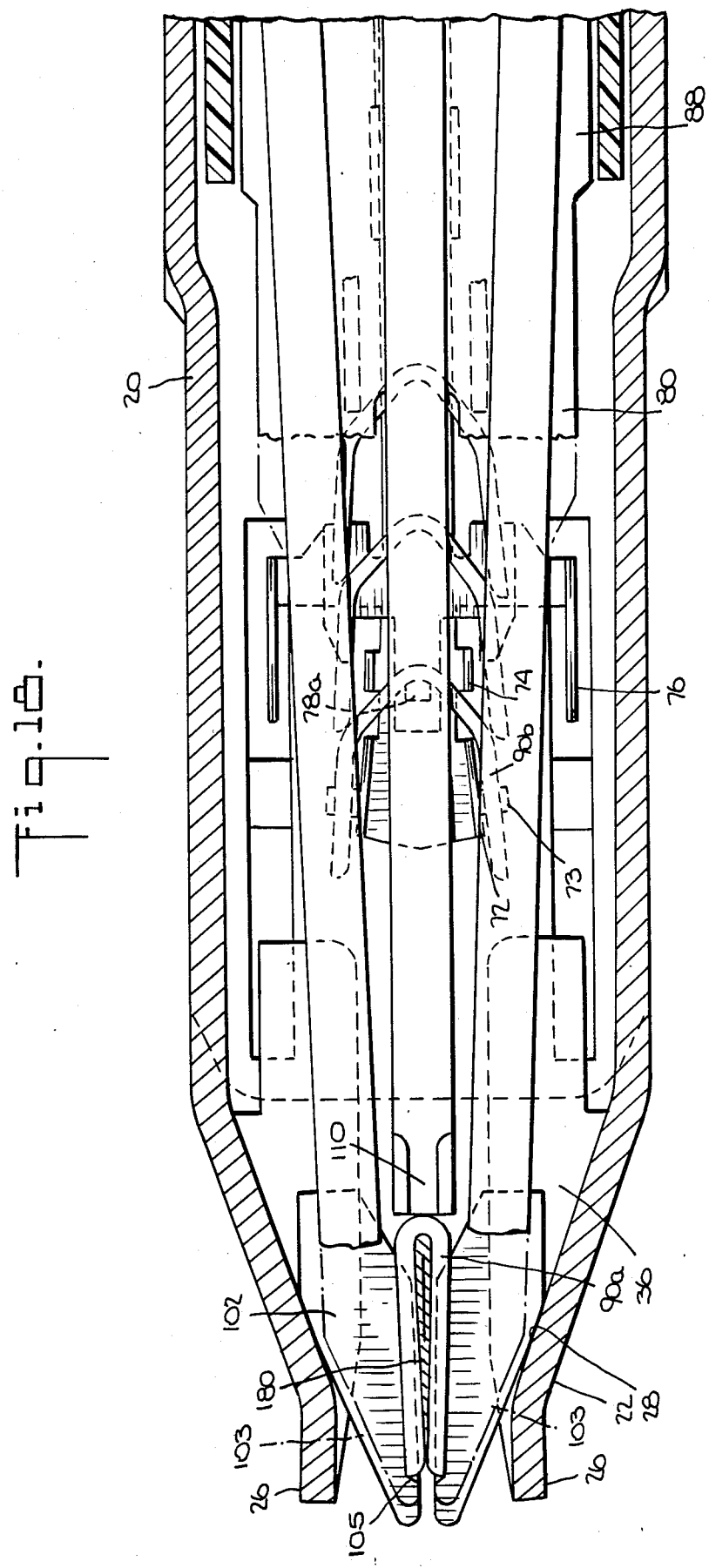
FIG. 18 is a view similar to FIG. 14 except that the peak clip closing position is shown.

FIG. 18 shows the apparatus at the end of the clip closing stroke, that is, when the ring handles are squeezed together most completely. Clip closing means 100 is at its distal-most position and jaws 103 are nearest to each other. This causes clip 90a to close completely around tubular structure 180. Jaws 103 protrude slightly beyond the distal end of longitudinal shaft 20. Thus, except for when the tips of the jaws 103 are at the end of the clip closing stroke, jaws 103 are retained within wrap plates 36 of the clip applier at all times. This protects the jaws against damage. Although not shown in FIG. 18, flaring 26 could extend sufficiently so that jaws 102 did not protrude beyond the distal end of longitudinal shaft 20 at any time.

Throughout the squeezing of the ring handles 140 during the clip closing stroke, clip closing means 100 carries with it spring 120. Distal end 122 of spring 120 contacts stationary rear surface 44 of track 40, causing spring 120 to be compressed. When the clip-closing stroke is completed, the surgeon stops squeezing together ring handles 140. Compressed spring 120 then tends to expand, thereby causing clip closing means 100 to move back to its original position, which in turn moves ring handles 140 apart through the linkage of pin 148.

FIGS. 19 and 25 are different views showing the condition of the apparatus when the return stroke is nearly complete. Jaws 103 move proximally and thus separate when they re-traverse the cam surfaces 28 in the proximal direction. Closed clip 90a slides out of the retreating jaws, a motion assisted by bevels 105 on the front inner surfaces of jaws 103 which cam proximally over the closed clip. Bevels 105 thus ensure that the closed clip does not become snagged on jaws 103.

As clip closing means 100 continues to move proximally, jaws 103 once more contact the apexes 77 of rearmost projections 76 of escapement 70. Jaws 103 cam escapement 70 down, out of the plane of the array of clips 90, so that projections 72 and 74 no longer confine clip 90b. Lift spring 78 lifts clip 90b so that it clears steps 106 and enters grooves 108 of jaws 103. Clip stop 110 moves proximally and contacts clip 90b. Lift spring tab 78a acts as a stop to prevent rearward motion of clip 90b when clip stop 110 passes over clip 90b as it continues to move proximally.

Spring 56 expands, causing clip follower 58 and clip array 90 to move distally until the apparatus reaches the condition shown in FIGS. 19 and 25. Continued rearward motion of means 100 will move clip 90b fully within jaws 103 where it is retained by jaw grooves 108 (comparable to the initial position of clip 90a as shown in FIGS. 14 and 20).

Clip applier 10 may now be withdrawn from tubular structure 180, which has been closed by compressed distal-most clip 90a. Clip applier 10 is then ready to be used to apply the next clip 90b to another tubular structure. This procedure can be repeated until the supply of clips has been exhausted.

In a preferred embodiment of this invention, a clutch assembly is used to ensure that each step in the clip closing and return cycle is completed before the next step is begun. FIGS. 26 and 27 illustrate the structure of the clutch assembly. This clutch may be used in any type of surgical device that applies surgical fasteners (e.g., surgical clips, surgical staples).

The clutch assembly includes clutch leaf spring 130, which lies partially within opening 112 in clip closing means 100. Clutch spring 130 is a resilient, substantially incompressible member and may be made of spring steel or any other material suitable for springs. The distal end 131 of clutch spring 130 is attached to projection 134 on clip closing means 100. The proximal end of clutch spring 130 includes clutch prong 132 with spur 133. One end of clutch prong 132 contacts projection 135, which extends for a short distance into opening 112 and then downward, away from the opening. Spur 133 extends over the portion of the clip closing means 100 adjacent to the proximal end of opening 112. That aids in fixing the vertical position of the proximal end of clutch spring 130. Blocks 48 and 49 extend longitudinally along and project from the inner surfaces of opposite sides of track 40.

The operation of the clutch assembly will now be described with reference to FIGS. 28-31. FIG. 28 shows the condition of the clutch assembly prior to the squeezing together of the ring handles 140. Clutch prong 132 is not in contact with blocks 48 or 49.

Figure 29:
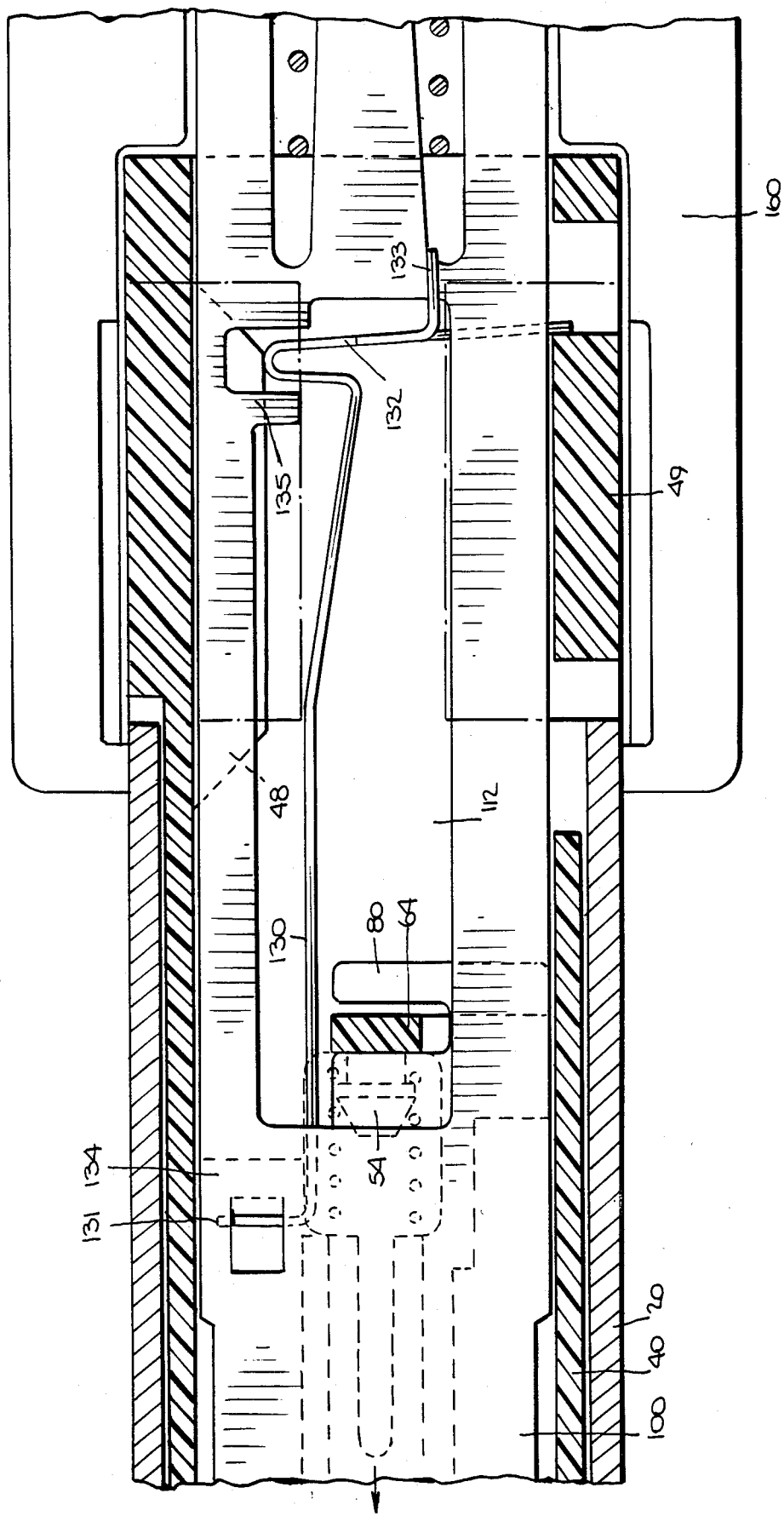
FIG. 29 is a view similar to FIG. 28 except that the clutch assembly is shown in a first intermediate distal position.

FIG. 29 shows the condition of the clutch assembly once the squeezing of the ring handles has begun. When a clip closing stroke is initiated, the clip closing means 100 moves in a distal direction. Clutch prong 132 contacts and traverses the proximal beveled surface of block 48 and then begins to traverse the flat surface of block 48. This motion causes the tip of clutch prong 132 to move toward and contact block 49. This position is shown in FIG. 29.

Figure 30:
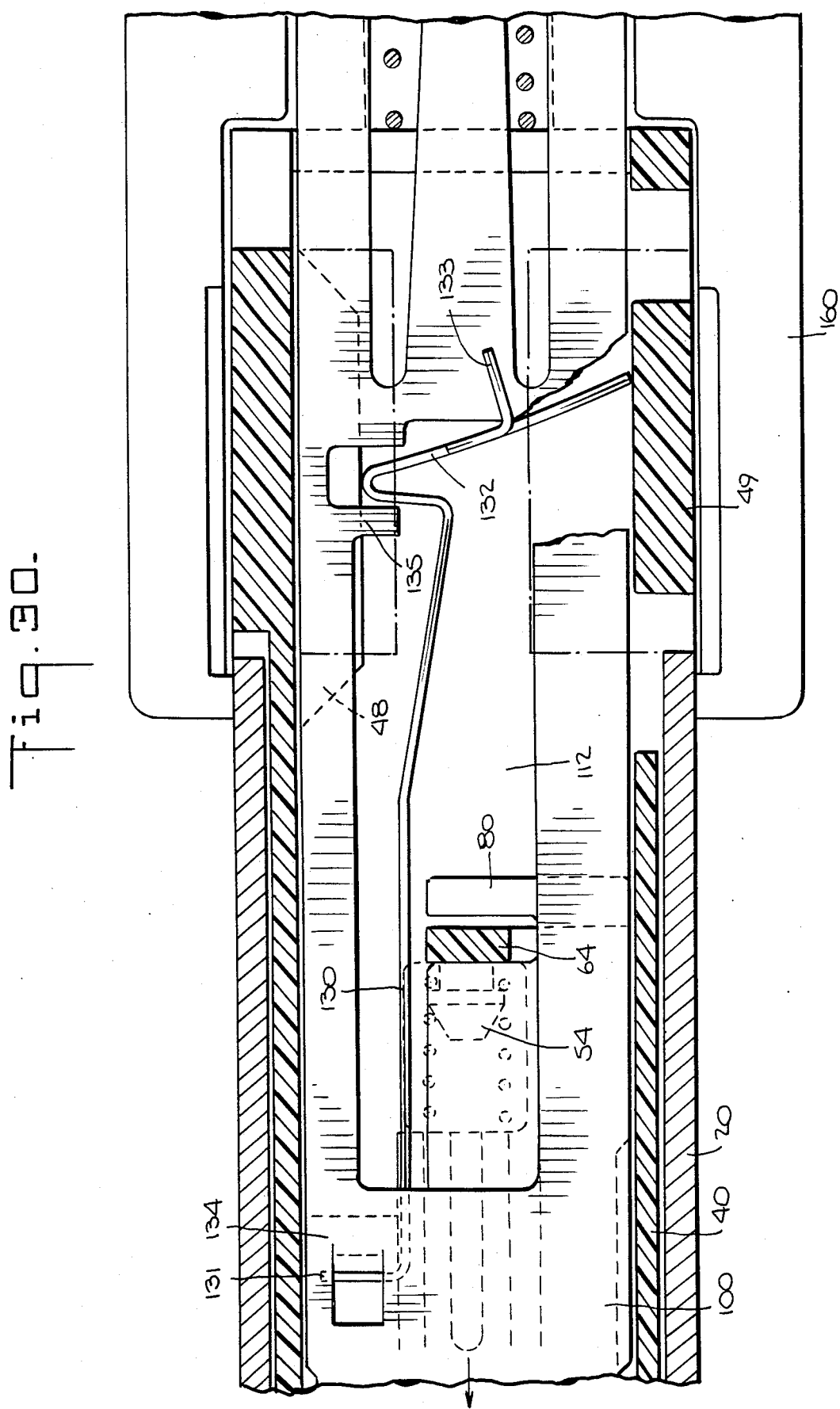
FIG. 30 is a view similar to FIG. 28 except that the clutch assembly is shown in a second intermediate distal position.

FIG. 30 shows the clutch assembly after further squeezing of ring handles 140. In this drawing, the clutch assembly is engaged. Clutch prong 132 travels distally along and is confined by blocks 48 and 49. The length of clutch prong 132 is greater than the lateral spacing between blocks 48 and 49. Therefore, this ensures that the tip of clutch prong 132 remains in contact with block 49 during the period that clutch prong 132 lies between blocks 48 and 49. Contact of clutch prong 132 with blocks 48 and 49 and projection 135 initially causes the tip of clutch prong 132 to move proximally with respect to the rest of the spring. The relative position of the tip is maintained as clutch prong 132 traverses blocks 48 and 49 during the clip closing stroke. If the surgeon ceases to squeeze ring handles 140 and thereby interrupts the clip-closing stroke, contact between spring 130 and blocks 48 and 49 will prevent return movement of the clip closing means 100. In particular, if return movement starts to occur, the tip of prong 132 digs into block 49 and stops such movement. Thus, the clutch assembly prevents partial closure of a clip.

Figure 31:
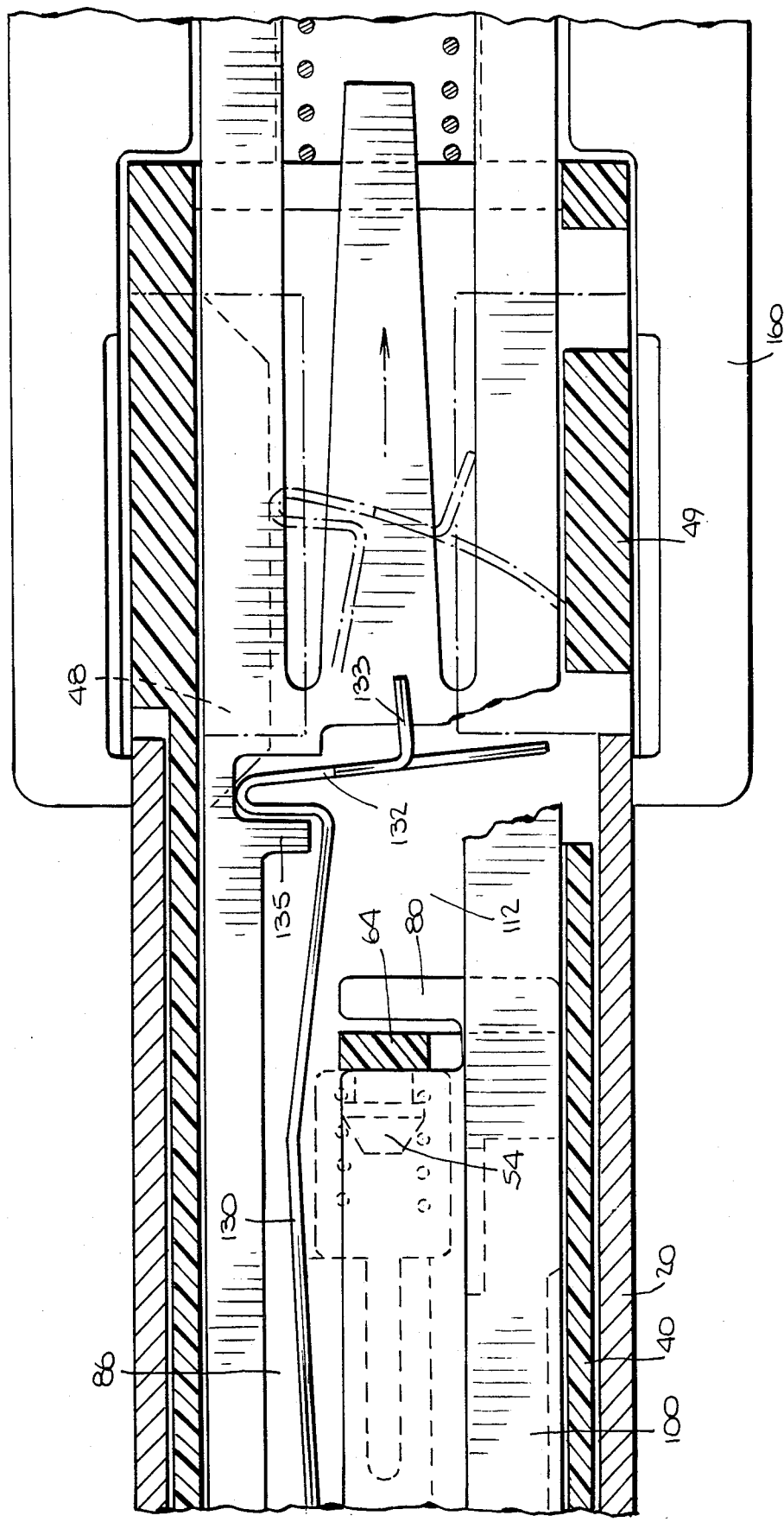
FIG. 31 is a view similar to FIG. 28 except that the clutch assembly is shown approaching the peak distal position and then in phantom is shown in an intermediate proximal position.

In FIG. 31, the clutch assembly is no longer engaged. Continued squeezing of ring handles 140 has caused further distal motion of clutch prong 132 so that it no longer contacts blocks 48 and 49. That allows all the force transmitted by squeezing the handles to be utilized for completing the closure of the clip. The cut-out in the proximal portion 86 of clip cover 80 provides clearance for the distal motion of clutch spring 130.

FIG. 31 also shows in phantom line the position of the clutch prong 132 during the return stroke when the clutch assembly is again engaged. During that stroke, contact of clutch prong 132 with blocks 48 and 49 and projection 135 causes the tip of clutch prong 132 to move distally with respect to the rest of the spring. If the surgeon attempts to squeeze ring handles 140 during the return stroke, contact between clutch prong 132 and blocks 48 and 49 will prevent distal movement by clip closing means 100. In particular, such distal movement would casue the tip of prong 132 to dig into block 49 and halt such movement. Thus, the clutch assembly prevents the initiation of a second clip closing stroke before the first return stroke is completed, thereby preventing clip jams.

It will be understood that the foregoing is only illustrative of the principles of the invention and that various modifications can be made by those skilled in the art without departing from the scope and spirit of the invention.

I claim:

1. Apparatus for applying surgical clips one at a time to body tissue, each clip having two legs joined together at a crown, said apparatus comprising:
    (a) a proximal portion;
    (b) a distal portion having stationary camming surfaces;
    (c) means for holding an array of surgical clips, the array having a distal end and a proximal end;
    (d) clip closing means for moving between distal and proximal positions and having at the distal end jaw means for (i) receiving the distal-most clip in the array and (ii) then moving towards the distal portion of the apparatus so that the jaw means contact the camming surfaces and close the clip around the body tissue; and
    (e) escapement means for (i) placing the distal-most clip of the array in the jaw means when the clip closing means has moved to the proximal position, which is towards the proximal portion of the apparatus, and (ii) preventing any of the other clips in the array from being placed in the jaw means at the same time, wherein the escapement means comprises three pairs of opposing projecting surfaces, which pairs point towards the plane of motion of the clip closing means and are spaced from one another in the longitudinal direction along the apparatus, the proximal-most pair of projecting surfaces extending beyond the middle pair of projecting surfaces in both the lateral and longitudinal directions, the escapement means being held stationary at its proximal end, the rest of the escapement means being able to move toward and away from the plane of motion of the clip closing means and being biased towards the plane, and the proximal-most pair of projecting surfaces resting against the clip closing means when those means are in the proximal position so that the middle and distal-most pair of projecting surfaces are out of the plane of motion of the clip closing means.

2. The apparatus of claim 1 wherein as the clip closing means moves towards the distal portion of the apparatus, the proximal-most pair of projecting surfaces can no longer rest on the clip closing means, thereby allowing the moveable portion of the escapement means to move towards the plane of motion of the clip closing means so that the middle and distal-most projecting surfaces confine and prevent motion of the next-to-distal-most clip as the distal-most clip is moved towards the camming surfaces of the distal portion of the apparatus.

3. The apparatus of claim 1 further comprising activating means for moving the clip closing means towards the camming surfaces.

4. The apparatus of claim 3 wherein the activating means comprises (a) a pair of rotatably mounted handles, each handle having an arcuate slot and the handles being mounted so that the curvatures of the two slots are not in the same direction, and (b) a pin attached to the clip closing means, the pin extending through both arcuate slots, the configuration being such that when the handles move towards each other, the point at which the pin extends through both slots moves in the distal direction, thereby moving the clip closing means in the distal direction.

5. The apparatus of claim 1 further comprising stop means for halting any movement in the proximal direction of the distal-most clip as it is being closed.

6. The apparatus of claim 5 wherein the stop means is attached to the clip closing means and moves along essentially the same line as the crown of the distal-most clip as that clip is moved towards the distal end of the apparatus.

7. The apparatus of claim 1 further comprising return means for moving the clip closing means towards its proximal position after the distal-most clip has been applied to body tissue.

8. The apparatus of claim 7 wherein the return means comprises a spring that is (a) normally expanded when not compressed and (b) is increasingly compressed as the clip closing means moves in a distal direction.

9. The apparatus of claim 1 further comprising clip advancing means for advancing the array of clips towards the position the jaw means occupies when the clip closing means is in its proximal position, thereby facilitating automatic feeding of the clips one at a time to the jaw means.

10. The apparatus of claim 9 wherein the clip advancing means comprises (a) a spring having proximal and distal ends, which spring is normally expanded when not compressed, the proximal end of the spring being held immovable in the apparatus, and (b) a movable clip follower that abuts the last clip in the array and is attached to the distal end of the spring, the expansion of the spring pushing the clip follower, which in turn pushes the entire array of clips.

11. The apparatus of claim 1 further comprising means for preventing significant movement of the jaw means in any but the longitudinal direction.

12. The apparatus of claim 1 further comprising a clutch which once it is engaged by the movement of the clip closing means in either the distal or proximal direction ensures that the direction of such movement is not reversed until the clutch is disengaged by sufficient movement of the clip closing means in the direction of movement that caused the clutch to engage.

13. The apparatus of claim 12 wherein the clutch comprises (a) first and second longitudinally disposed, laterally spaced plastic portions, and (b) a piece of resilient metal fastened at a first end to the clip closing means and formed so that when the clutch is engaged the second end of the piece of metal is forced by contact of part of the piece of metal with the first plastic portion against the second plastic portion at an acute angle, the second end of the piece of metal (a) sliding along the second plastic portion when the clip closing means moves in the direction that caused the clutch to engage but (b) firmly engaging the second plastic portion when the clip closing means attempts to move in the other direction.

* * * * *